United States Patent
Fujii

(10) Patent No.: US 10,485,523 B2
(45) Date of Patent: Nov. 26, 2019

(54) DISSECTING DEVICE

(71) Applicant: TERUMO KABUSHIKI KAISHA, Shibuya-ku, Tokyo (JP)

(72) Inventor: Tatsunori Fujii, Kanagawa (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 354 days.

(21) Appl. No.: 15/443,696

(22) Filed: Feb. 27, 2017

(65) Prior Publication Data
US 2017/0245845 A1 Aug. 31, 2017

(30) Foreign Application Priority Data
Feb. 29, 2016 (JP) .................... 2016-038088

(51) Int. Cl.
*A61B 18/14* (2006.01)
*A61B 17/00* (2006.01)
(Continued)

(52) U.S. Cl.
CPC .... *A61B 17/00008* (2013.01); *A61B 18/1482* (2013.01); *A61B 1/313* (2013.01);
(Continued)

(58) Field of Classification Search
CPC ...... A61B 17/00008; A61B 17/320016; A61B 18/1482; A61B 2017/00013;
(Continued)

(56) References Cited

U.S. PATENT DOCUMENTS 5,667,480 A * 9/1997 Knight ............... A61B 1/018
128/898
6,193,653 B1 * 2/2001 Evans ............. A61B 17/00008
600/210
(Continued)

FOREIGN PATENT DOCUMENTS

JP 2003-190171 A 7/2003
JP 2005-246058 A 9/2005
JP 2006-000485 A 1/2006

OTHER PUBLICATIONS

Office Action (Notice of Reasons for Refusal) dated Jul. 10, 2019, by the Japanese Patent Office in corresponding Japanese Patent Application No. 2016-038088 and an English Translation of the Office Action. (8 pages).

*Primary Examiner* — Michael F Peffley
(74) *Attorney, Agent, or Firm* — Buchanan Ingersoll & Rooney PC

(57) ABSTRACT

A dissecting device that includes a grasping section and a dissecting member. The grasping section has an insertion lumen that permits an imaging device to be positioned therein. The dissecting member is at the distal portion of the grasping section and is insertable into a living body and movable along a blood vessel to dissect tissue surrounding the blood vessel. The dissecting member includes a base part having a lumen that communicates with the insertion lumen and a dissecting section which extends distally from the base part. The dissecting section is configured to dissect the tissue in the living body when the dissecting member is moved along the blood vessel. The dissecting member includes a blood vessel guide passage that accepts a branch vessel branched from the blood vessel at the distal portion of the dissecting member and guides the branch vessel toward the base part.

16 Claims, 17 Drawing Sheets

(51) Int. Cl.
   *A61B 1/313*     (2006.01)
   *A61B 17/32*     (2006.01)
   *A61B 18/00*     (2006.01)
   *A61B 90/00*     (2016.01)

(52) U.S. Cl.
   CPC ..... *A61B 17/320016* (2013.01); *A61B 90/361* (2016.02); *A61B 2017/00013* (2013.01); *A61B 2017/00778* (2013.01); *A61B 2017/320044* (2013.01); *A61B 2018/00589* (2013.01); *A61B 2018/00595* (2013.01)

(58) Field of Classification Search
   CPC ......... A61B 2017/320044; A61B 2017/00778; A61B 2017/320052; A61B 2018/00595; A61B 2018/00428; A61B 2018/00589; A61B 1/313
   See application file for complete search history.

(56) References Cited

U.S. PATENT DOCUMENTS

| | | | | |
|---|---|---|---|---|
| 6,527,771 | B1 * | 3/2003 | Weadock | A61B 17/00008 606/170 |
| 6,656,176 | B2 * | 12/2003 | Hess | A61B 17/00008 600/104 |
| 7,314,479 | B2 * | 1/2008 | Wellman | A61B 17/22031 606/205 |
| 7,981,127 | B2 | 7/2011 | Kasahara et al. | |
| 8,052,702 | B2 * | 11/2011 | Hess | A61B 17/00008 600/104 |
| 2003/0130674 | A1 | 7/2003 | Kasahara et al. | |
| 2005/0192613 | A1 | 9/2005 | Lindsay | |
| 2006/0206112 | A1 | 9/2006 | Kasahara | |

* cited by examiner

DISSECTING DEVICE

CROSS-REFERENCES TO RELATED APPLICATIONS

This application claims priority to Japanese Application No. 2016-038088 filed on Feb. 29, 2016, the entire content of which is incorporated herein by reference.

DESCRIPTION

The present disclosure generally relates to a dissecting device for dissecting tissue such as fat in a living body.

It is widely known to use an artery graft represented by internal thoracic artery, gastroepiploic artery and radial artery or a vein graft represented by great saphenous vein as a bypass vessel in performing vascular bypass grafting at the heart (coronary artery bypass grafting: CABG). It has also been reported that artery grafts (particularly, internal thoracic artery) offer higher long-term patency rates than vein grafts.

Vein grafts are commonly deemed to be poor in long-term patency rate. In recent years, however, it has been reported that the long-term patency rate concerning a vein graft is enhanced when the vein graft is harvested when being covered with the surrounding tissue (for example, fat, connective tissue, tissue between a skin layer and a muscle layer, tissue between a skin layer and an interosseous membrane, branch vessels, etc.) and is used as a bypass vessel while remaining covered with the tissue.

U.S. Pat. No. 7,981,127 discloses a system to endoscopically harvest a blood vessel in a living body.

SUMMARY

In the system disclosed in U.S. Pat. No. 7,981,127, however, a blood vessel and the surrounding tissue (fat) are first dissected by a dissecting device (dissector 3), and then a branch vessel exposed in the living body is stanched and cut by a cutting device (treatment sheath 2). The system of U.S. Pat. No. 7,981,127 is not configured to enable a blood vessel to be harvested together with the surrounding tissue. This system additionally has a drawback in that the stanching and cutting may be conducted by capturing the branch vessel exposed in the living body, and, therefore, workability (i.e., operability) in harvesting the blood vessel is poor.

The dissecting device disclosed here permits a blood vessel to be harvested (i.e., extracted or removed from the living body) together with the surrounding tissue with good workability.

In one aspect, there is provided a dissecting device including: a grasping section which has an insertion lumen permitting an imaging device to be inserted therein and which is adapted to be graspable by a user; and a dissecting member provided at a distal portion of the grasping section, wherein the dissecting member includes a base part having a lumen communicating with the insertion lumen, a dissecting section which extends distally from the base part and which, when being inserted into a living body along a blood vessel, dissects tissue in the living body, and a blood vessel guide passage by which a branch vessel branched from the blood vessel is accepted from a distal portion of the dissecting member and is guided toward the base part side. In another aspect, a dissecting device is disclosed that includes a grasping section and a dissecting member. The grasping section has an insertion lumen that permits an imaging device to be positioned therein. The dissecting member is at the distal portion of the grasping section and is insertable into a living body and movable along a blood vessel to dissect tissue surrounding the blood vessel. The dissecting member includes a base part having a lumen that communicates with the insertion lumen and a dissecting section which extends distally from the base part. The dissecting section is configured to dissect the tissue in the living body when the dissecting member is moved along the blood vessel. The dissecting member includes a blood vessel guide passage that accepts a branch vessel branched from the blood vessel at the distal portion of the dissecting member and guides the branch vessel toward the base part.

According to this configuration of the dissecting device, providing the dissecting member with the blood vessel guide passage helps ensure that when the dissecting device is inserted into a living body along a blood vessel, it is possible to dissect tissue in the living body and to easily capture a branch vessel embedded in the tissue. Consequently, a treatment of stanching and cutting a branch vessel can be easily performed while observing the captured branch vessel by the imaging device inserted in the insertion lumen.

In the dissecting device, the blood vessel guide passage may be thinner (smaller in diametric size) than the insertion lumen.

This configuration makes it possible to reduce the amount of the tissue surrounding the branch vessel captured by the blood vessel guide passage. As a result, visibility of the branch vessel by the imaging device is enhanced to facilitate the stanching and cutting treatment of the branch vessel.

In the dissecting device, the dissecting section may be configured such that its thickness in a height direction perpendicular to a longitudinal direction of the dissecting device increases in a proximal direction.

This configuration enables the tissue in the living body to be dissected effectively.

In the dissecting device, the blood vessel guide passage may have a length from the dissecting section to a distal end wall of the base part.

The blood vessel guide passage of the dissecting device may be configured such that its height in a direction perpendicular to the longitudinal direction of the dissecting device increases. The height increase of the blood vessel guide passage may be in proportion (proportional) to the increase in the proximal direction of the thickness of the dissecting section in the height direction (perpendicular to the longitudinal direction) of the dissecting device.

In the dissecting device, a width of a proximal portion of the blood vessel guide passage may be smaller than a width of a distal portion of the blood vessel guide passage.

This configuration enables the surrounding tissue to be effectively dissected from the branch vessel.

In the dissecting device, the blood vessel guide passage may include a first guide passage, a second guide passage on a proximal side of the first guide passage at a position different from the position of the first guide passage in a width direction (perpendicular to the longitudinal direction) of the dissecting device, and an intermediate guide passage interconnecting the first guide passage and the second guide passage.

According to this configuration, the surrounding tissue can be dissected from the branch vessel more effectively when the branch vessel is guided by the blood vessel guide passage because the blood vessel guide passage is crooked (i.e., bent, uneven or non-parallel).

The dissecting device may include an introducing section at a distal portion of the blood vessel guide passage. The width of the introducing section may decrease in the proximal direction, and the width of the introducing section may be not less than the width of the blood vessel guide passage (i.e., the width of the introducing section may be equal or greater than the width of the blood vessel guide passage).

This configuration enables easy guide of the branch vessel into the blood vessel guide passage.

In the dissecting device, the dissecting member may include a roof section which covers the blood vessel guide passage and the dissecting section at least partly and which permits the branch vessel to pass between the roof section and the dissecting section.

This configuration ensures that when the branch vessel is guided by the blood vessel guide passage, the tissue surrounding the branch vessel can be separated by the roof section. Therefore, the tissue is prevented or restrained from entering into a proximal portion of the blood vessel guide passage. Consequently, the visibility of the branch vessel by the imaging device is enhanced, and the stanching and cutting treatment of the branch vessel can be performed more efficiently.

In the dissecting device, a treating section configured to stanch and cut the branch vessel may be provided at a proximal portion of the blood vessel guide passage.

Capturing, stanching and cutting the branch vessel can thus be performed through a simple operation of moving the dissecting device forward and outputting (supplying) energy to the treating section.

In yet another aspect, a dissecting device for dissecting tissue surrounding a blood vessel in a living body is disclosed. The blood vessel includes a branch vessel branching outwardly away from the blood vessel. The dissecting device includes an elongated tubular body having an insertion lumen configured to permit an imaging device to be positioned in the insertion lumen. The elongated tubular body is graspable by a user. The dissecting device also includes a dissecting member connected to the distal portion of the elongated tubular body. The dissecting member is insertable into the living body and movable along the blood vessel to dissect the tissue surrounding the blood vessel. The dissecting member includes a base part and two protruding parts extending distally from the base part. The two protruding parts are spaced apart from one another in the lateral direction to create a blood vessel guide passage between the two protruding parts. The blood vessel guide passage includes a tapered portion and a straight portion proximal of the tapered portion. The inner surface of one protruding part is spaced apart from the inner surface of the other protruding part in the lateral direction. The distance between the inner surface of the one protruding part and the inner surface of the other protruding part gradually decreases throughout the tapered portion of the blood vessel guide passage from the distal end of the two protruding parts to the proximal end of the tapered portion. The distance between the inner surfaces of the protruding parts is constant along the straight portion of the blood vessel guide passage from the distal end of the straight portion to the proximal end of the straight portion. The dissecting member includes a treating section at the proximal end of the straight portion of the blood vessel guide passage. The treating section includes two electrodes and a cutting section. The two electrodes are configured to stanch the branch vessel and the cutting section is configured to cut the branch vessel. The blood vessel guide passage of the dissecting member is configured to accept the branch vessel branched from the blood vessel at the tapered portion of the blood vessel guide passage and guide the branch vessel through the straight portion of the blood vessel guide passage to the treating section when the dissecting member is moved along the blood vessel.

In another aspect, this application relates to a dissecting method for dissecting tissue surrounding a blood vessel in a living body. The method includes introducing a dissecting device into the living body by way of an incision. The dissecting device has a main body, two protruding portions, a stanching section and a cutting section. The two protruding portions protrude distally beyond the main body in the longitudinal direction of the main body. The method also includes positioning the dissecting device below the blood vessel in the living body, the stanching section and the cutting section being at a bottom of the dissecting device in the thickness direction of the dissecting device so that the stanching section and the cutting section are below the blood vessel and spaced apart from the blood vessel, and dissecting the tissue surrounding the blood vessel in the living body by moving the dissecting device forward along the blood vessel while the dissecting device is below the blood vessel. The blood vessel includes branch vessels that branch outwardly away from the blood vessel. The method further includes guiding one of the branch vessels toward the stanching section using the two protruding portions, stanching the branch vessel using the stanching section of the dissecting device, and cutting the branch vessel from the blood vessel using the cutting section of the dissecting device after the stanching of the branch vessel.

In accordance with the dissecting device and dissecting method disclosed in this application, it is possible, at the time of harvesting a blood vessel together with the surrounding tissue, to easily capture branch vessels embedded in the tissue and to easily perform a stanching and cutting treatment of the branch vessels. The dissecting device also possesses good workability (e.g., operability).

DETAILED DESCRIPTION OF THE PREFERRED EMBODIMENTS

Set forth below with reference to the accompanying drawings is a detailed description of embodiments of a dissecting device and a dissecting method representing examples of the inventive dissecting device and dissecting method disclosed here.

[General Configuration of Dissecting System 10]

Figure 1:
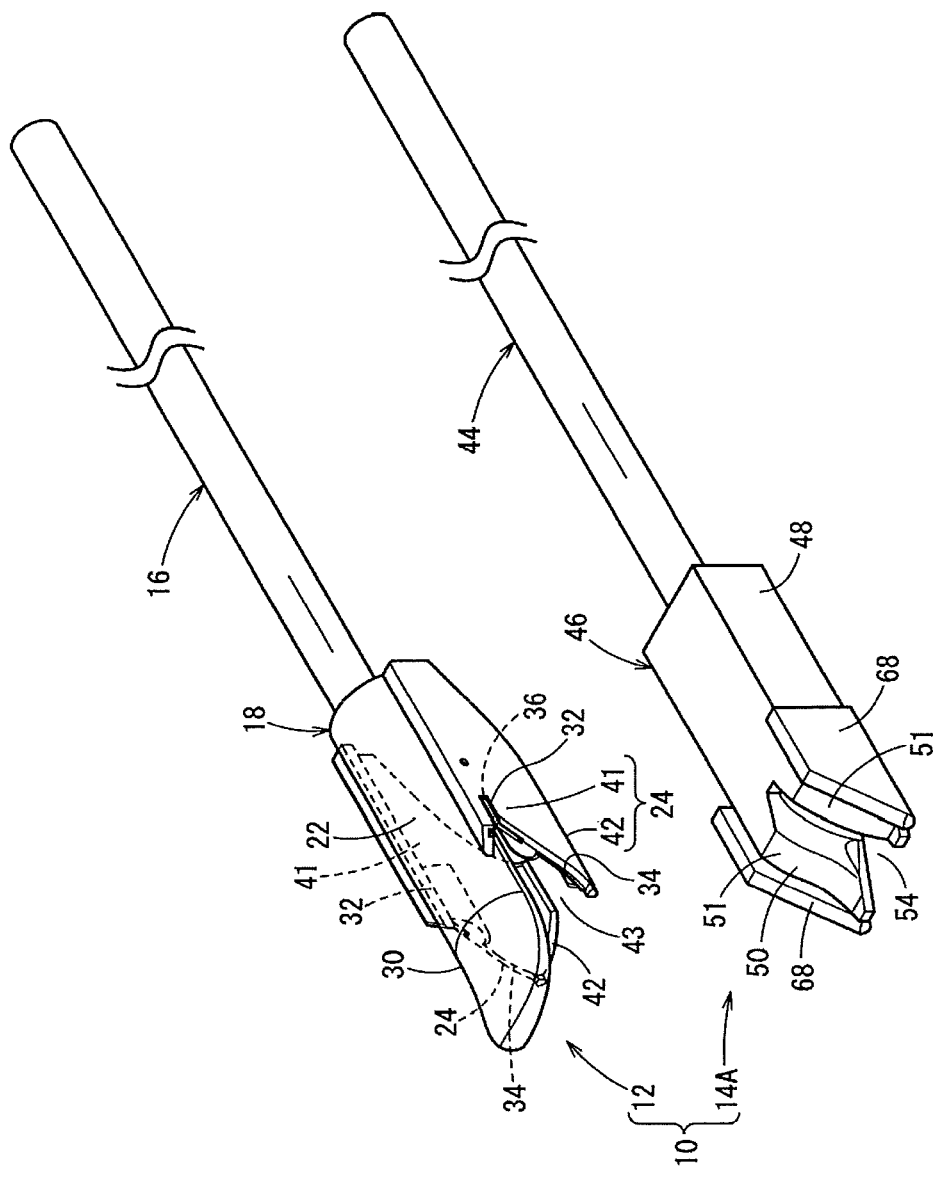
FIG. 1 is a perspective view of a dissecting system.

A dissecting system 10 shown in FIG. 1 is a device used to harvest a blood vessel for use as a bypass vessel in carrying out blood vessel bypass grafting (particularly, coronary artery bypass grafting: CABG). The dissecting system 10 can harvest a blood vessel when the blood vessel is covered with surrounding tissue (fat, connective tissue, etc.). The blood vessel to be harvested using the dissecting system 10 is not particularly limited so long as it is a blood vessel that can be used as a bypass vessel. Examples of an applicable blood vessel include internal thoracic artery, gastroepiploic artery, radial artery, and saphenous veins (great saphenous vein and small saphenous vein).

In a preferred embodiment, the blood vessel to be harvested is a saphenous vein. The use of the dissecting system 10 facilitates harvesting of a blood vessel in the state in which the blood vessel is covered with the surrounding tissue. When a saphenous vein is harvested by use of the dissecting system 10 and is used as a bypass vessel, an enhanced long-term patency rate is obtained after the bypass grafting.

The dissecting system 10 includes two kinds of dissecting devices 12 and 14A. Hereinafter, one of the two dissecting devices 12 and 14A will be referred to as "the first dissecting device 12," and the other will be referred to as "the second dissecting device 14A." Both the first dissecting device 12 and the second dissecting device 14A are each an elongated device configured to be inserted into a living body along a blood vessel such as a saphenous vein.

[Configuration of First Dissecting Device 12]

Figure 2:
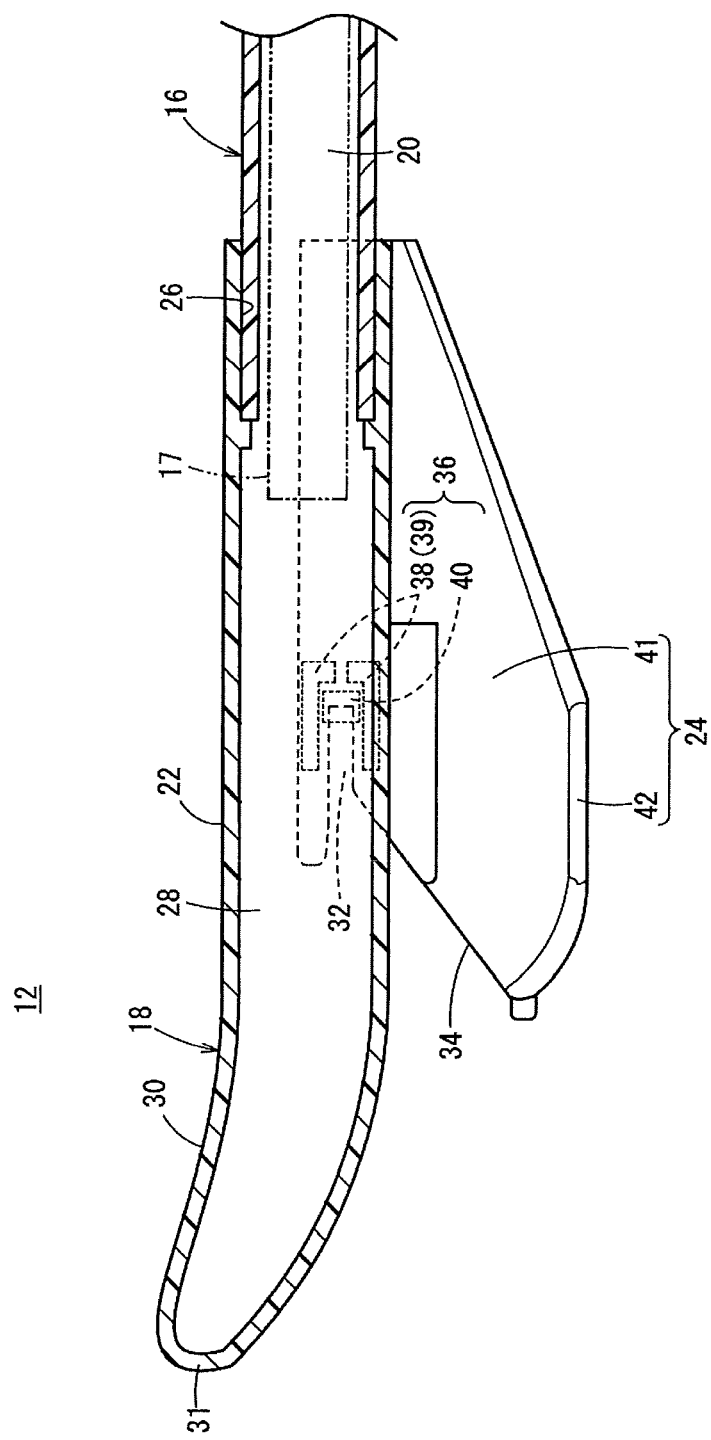
FIG. 2 is a sectional view of a distal portion of a first dissecting device.

The first dissecting device 12 includes a grasping section 16 adapted (configured) to be graspable by a user (e.g., a technician or an operator), and a dissecting member 18 provided at a distal portion of the grasping section 16. As depicted in FIG. 2, the grasping section 16 is a tubular member (e.g., a cylindrical body) possessing an insertion lumen 20 in which an imaging device 17 (for example, an endoscope) can be inserted. The grasping section 16 in the illustrated example is formed in a rectilinear shape. Examples of materials of the grasping section 16 include rigid resins and metals.

The insertion lumen 20 is a through-hole which extends along, a longitudinal direction of the grasping section 16. The insertion lumen 20 opens at a distal surface and a proximal surface of the grasping section 16 (i.e., the distal-most end and the proximal-most end of the insertion lumen 20 are open). An objective lens and an illuminating portion, for example, may be located at the distal portion of the imaging device 17.

The dissecting member 18 includes a hollow-structured base section 22 (first dissecting section) which is fixed to a distal portion of the grasping section 16. The dissecting member 18 also includes a pair of side sections 24 (second dissecting section) projecting from both sides in a width direction of the base section 22 toward one side (lower side in FIG. 1) in a thickness direction of the base section 22. The base section 22 has a flattened cross-sectional shape which is relatively short in the vertical direction and relatively long in the width direction (i.e., the length of the base section 22 in the width direction may be greater than the length of the base section 22 in the thickness direction). The width of the base section 22 is greater than the outside diameter of a blood vessel to be harvested (i.e., the target blood vessel).

As shown in FIG. 2, the base section 22 includes a fixing hole 26 in which a distal portion of the grasping section 16 is fixed (i.e., attached or connected). and the base section 22 also includes a cavity 28 which extends from a position slightly distal of the fixing hole 26 to the vicinity of the distal end of the base section 22. The cavity 28 communicates with the insertion lumen 20.

The base section 22 possesses a distal dissecting section 30 at the distal portion of the base section 22. The dissecting section 30 dissects tissue. The distal dissecting section 30 is tapered distally (i.e., the outer diameter of the distal dissecting section 30 decreases towards the distal-most end of the base section 22), for easy dissection of tissue. Specifically, the distal dissecting section 30 is formed in such a shape that the length in a minor axis direction and the length in a major axis direction of its cross-sectional shape gradually decrease in the distal direction (i.e., towards the distal end 31 of the distal dissecting section 30). A distal end 31 (apex portion or distal-most end) of the distal dissecting section 30 is formed in a rounded shape to prevent the distal dissecting section 30 from damaging a blood vessel to be harvested or branch vessel. The distal dissecting section 30 is also curved such that the distal dissecting section 30 gradually extends or protrudes upward from a base portion located on the proximal side of the distal dissecting section 30 (i.e., the distal dissecting section 30 curves upwards in the thickness direction relative to the grasping section 16).

The base section 22 is formed of a transparent (light-transmitting) material (for example, glass, transparent resin or the like). With the imaging device 17 inserted in the insertion lumen 20 and the cavity 28, it is possible to image the front side and the surroundings of the base section 22 for observation (visual confirmation) by the imaging device 17. The base section 22 preferably is substantially colorless and transparent, but the base section 22 may be colored as long as it is transparent.

The pair of side sections 24 are sections (members) for dissecting tissue on both lateral sides under the base section 22. The pair of side sections 24 are provided at near-proximal-end portions on both lateral sides of the base section 22. Therefore, the base section 22 (which includes the distal dissecting section 30) protrudes distally beyond the pair of side sections 24.

As illustrated in FIG. 1, each of the pair of side sections 24 is provided with a groove section 32 into which a branch vessel 73 (see FIG. 5, etc.) branched from a blood vessel 72 can be accepted. Each of the pair of side sections 24 also includes a guide section 34 which is continuous with a distal end of the groove section 32. The guide section 34 guides the branch vessel 73 into the groove section 32. The groove section 32 is a rectilinear groove that extends along the longitudinal direction of the dissecting member 18, and penetrates the side section 24 in the thickness direction of the side section 24 (i.e., the width direction of the base section 22). The width (the dimension measured in the height direction of the dissecting member 18) of the groove section 32 may be constant along the lengthwise direction of the groove section 32 or may gradually decrease in the proximal direction (i.e., taper towards the proximal-most end of the groove section 32).

A treating section 36 for stanching and cutting the branch vessel 73 is provided at the groove section 32 as illustrated in FIG. 2. The treating section 36 includes a stanching section 38 for stanching the branch vessel 73, and a cutting section 40 (e.g., a cutting edge) for cutting the branch vessel 73. The stanching section 38 has a bipolar structure including a pair of electrodes 39. The pair of electrodes 39 are provided respectively on both sides in the width direction of the groove section 32. When a branch vessel 73 is guided into the groove section 32, the branch vessel 73 can be stanched by thermal coagulation by applying a high-frequency voltage between the pair of electrodes 39. The cutting section 40 is provided proximally of the distal ends of the pair of electrodes 39. The branch vessel 73 can be cut by the cutting section 40 after the branch vessel 73 has undergone thermal coagulation based on this configuration.

The guide section 34 is inclined toward the groove section 32 side, at a distal portion of the side section 24. Specifically, the guide section 34 is inclined towards the base section 22 side from the distal end to the proximal end of the guide section 34 as illustrated in FIG. 1. The guide section 34 is configured in this manner to help ensure that when the dissecting member 18 is moved forward along the target blood vessel 72 (i.e., the blood vessel 72 to be harvested), the branch vessel 73 can be lifted up and smoothly guided toward the groove section 32 side.

Each of the pair of side sections 24 includes a side wall portion 41 extending from the base section 22 as illustrated in FIG. 1. Each of the pair of side sections 24 also includes a pair of projecting portions 42 projecting toward the inside (i.e., towards the center of the dissecting member 18 in the width direction) from the side wall portion 41, opposite the base section 22. The groove section 32 and guide section 34 described above are provided in the side wall portion 41.

Projecting ends of the pair of projecting portions 42 are opposite to each other. A space 43 is between the pair of projecting portions 42 to permit the branch vessel 73 to pass therethrough. The pair of projecting portions 42 help ensure that when the dissecting member 18 is moved forward along the blood vessel 72 to be harvested, tissue (excluding the portion of the tissue in the space 43) located on the opposite side of the blood vessel 72 from the base section 22 can be dissected.

[Configuration of Second Dissecting Device 14A]

The second dissecting device 14A includes a grasping section 44 adapted (configured) to be graspable by the user, and a dissecting member 46 provided at a distal portion of the grasping section 44. As depicted in FIG. 3B, the grasping section 44 is a tubular member having an insertion lumen 45. An imaging device 17 can be inserted into the insertion lumen 45 (i.e., an imaging device is insertable into the insertion lumen 45 of the grasping section 44). The grasping section 44 in the illustrated example possesses a rectilinear shape. Examples of the grasping section 44 material include rigid resins and metals. The insertion lumen 45 is a through-hole which extends along the longitudinal direction of the grasping section 44. The insertion lumen 45 is open at a distal surface and a proximal surface of the grasping section 44 (i.e., the insertion lumen 45 is open at the distal-most and proximal-most ends of the grasping section 44).

The dissecting member 46 includes a base part 48 fixed to a distal portion of the grasping section 44 and a dissecting section 50 extending distally from a distal end of the base part 48. The base part 48 is formed in a hollow shape. The base part 48 has a lumen 49 which extends along the longitudinal direction of the dissecting member 46. The distal end of the lumen 49 is closed by a distal end wall 48a of the base part 48. As indicated by an imaginary line in FIG. 3B, a front surface of the distal end wall 48a of the base part 48 may be an inclined surface 48b. The inclined surface 48b is inclined to be displaced toward the upper side (skin side) in the proximal direction (i.e., the inclined surface 48b is between a lower edge of the base part and an upper edge of the base part, such that the lower edge extends distally of the upper edge as shown in FIG. 3B). A proximal end of the lumen 49 is open at a proximal surface (i.e., proximal-most end) of the base part 48. The inner diameter of the lumen 49 is greater than the outer diameter of the grasping section 44. A distal portion of the grasping section 44 is inserted and fixed at a proximal-side region of the lumen 49 (i.e., the outer surface of the grasping section 44 is fixed/attached to the inner surface of the base part 48 at a proximal portion of the lumen 49). The lumen 49 has a cavity 49a on the distal side of the grasping section 44. A distal portion of the imaging device 17 can enter (is insertable) into the cavity 49a.

The base part 48 in the illustrated example has a cross-sectional profile which is tetragonal in shape. The cross-sectional profile of the base part 48 may be a shape other than a tetragon, such as a circle, an ellipse, or a trapezoid.

The dissecting member 46 (particularly, the base part 48) is transparent (light-transmitting). Examples of the dissecting member 46 material include glass and transparent resin. With a transparent base part 48, it is possible to image the front side (i.e., the distal side) and the surroundings of the base part 48 for observation by the imaging device 17 when the imaging device 17 is inserted in the insertion lumen 45. At a distal portion of the insertion lumen 45, a light reflection preventing section may be provided in the state of being oriented toward a blood vessel guide passage 54. The light reflection preventing section prevents a visual field from being obstructed due to reflection of light of an endoscope. The light reflection preventing section may be integral with or separate from the insertion lumen 45. The light reflection preventing section is formed, for example, from a low-reflectance material or a transparent resin. The light reflection preventing section can be positioned at an angle relative to a longitudinal axis of the endoscope such that the light reflection preventing section is not perpendicular to a light source of the endoscope.

Although it is preferable that the dissecting member 46 is substantially colorless and transparent, the dissecting member 46 may be colored as long as it is transparent. The dissecting member 46 may not necessarily be entirely transparent. For example, only the base part 48 (particularly, only the distal end wall 48*a* functioning as an observation window) may be transparent. The distal end wall 48*a* of the dissecting member 46 may not necessarily be a portion formed integrally with the other portions of the dissecting member 46. The distal end opening of the cavity 49*a* may thus be closed with a separate transparent member.

Figure 3A:
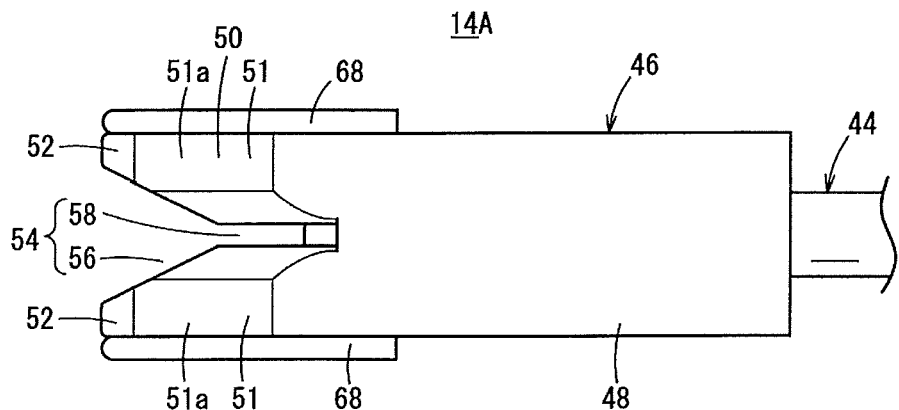
FIG. 3A is a plan view of a distal portion of a second dissecting device.
Figure 3B:
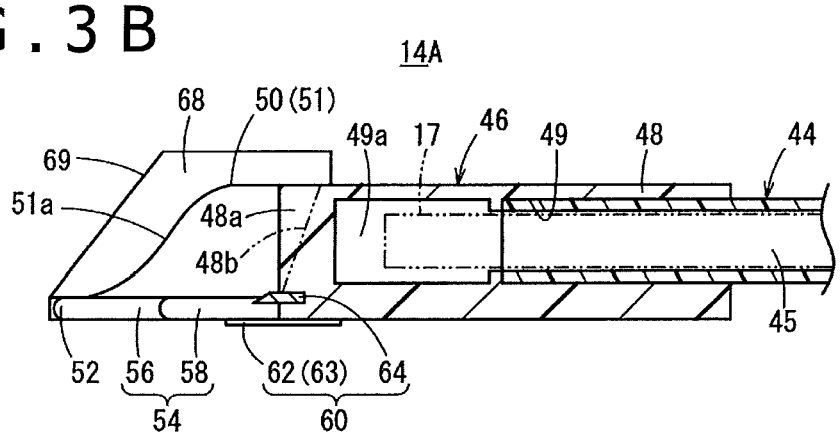
FIG. 3B is a sectional view of the distal portion of the second dissecting device.

As illustrated in FIGS. 1 and 3A, the dissecting section 50 includes a pair of dissecting portions 51 which dissect tissue (fat 74 or the like) when the dissecting member 46 is moved forward along a blood vessel 72. The pair of dissecting portions 51 are spaced apart in the width direction of the dissecting member 46. "The width direction of the dissecting member 46" means a direction which is perpendicular to the axial direction (longitudinal direction) of the dissecting device 14A and which is perpendicular to the thickness direction of the dissecting member 46 (the direction in which the dissecting member 46 dissects the fat 74; the vertical direction in FIG. 3B). The thickness (the dimension measured in the height direction of the dissecting member 46) of each dissecting portion 51 gradually increases in the proximal direction so that tissue is easily dissected in the direction of alignment of the blood vessel 72 with the dissecting member 46. Specifically, each dissecting portion 51 has an inclined surface 51*a* that is inclined to be displaced toward the upper side (the skin side) in the proximal direction (i.e., the lower edge of the inclined surface 51*a* is distal to the upper edge of the inclined surface 51*a* and the inclined surface 51*a* extends between the lower and upper edges as shown in FIGS. 1 and 3B). In addition, the distal end of the dissecting portion 51 is located distal to the distal end of the base part 48. Each dissecting portion 51 includes a projection 52 projecting distally from a distal portion of the dissecting portion 51, for enabling easy dissection of tissue.

The dissecting member 46 includes the blood vessel guide passage 54 at the distal portion of the dissecting member 46. The blood vessel guide passage 54 accepts and guides a branch vessel 73 toward the base part 48 side (i.e., proximally). The blood vessel guide passage 54 is formed between the pair of dissecting portions 51 described above. The blood vessel guide passage 54 penetrates the dissecting member 46 in the thickness direction of the dissecting member 46. Therefore, the blood vessel guide passage 54 is an opening in the distal direction of the dissecting member 46, and is open to the upper side of the dissecting member 46 and to the lower side of the dissecting member 46. A front surface of the distal end wall 48*a* of the base part 48 faces (is opposite to) a proximal portion of the blood vessel guide passage 54. The height of the blood vessel guide passage 54 (perpendicular to the longitudinal direction of the dissecting device 14A) increases in proportion to the increase of the thickness of the dissecting section 50 from the distal end to the proximal end of the dissecting section 50 in the height direction (perpendicular to the longitudinal direction of the dissecting device 14A).

The blood vessel guide passage 54 includes a first groove section 56 (introducing section) constituting a distal-side region of the blood vessel guide passage 54 and a second groove section 58 constituting a proximal-side region of the blood vessel guide passage 54. The first groove section 56 possesses a width which decreases in the proximal direction (i.e., the width of the first groove section 56 gradually decreases between the distal end of the first groove section 56 and the proximal end of the first groove section 56). The width of the first groove section 56 is greater than the width of the second groove section 58. The second groove section 58 is a rectilinear groove which communicates with the first groove section 56 and which extends along the longitudinal direction of the dissecting member 46.

Figure 3C:
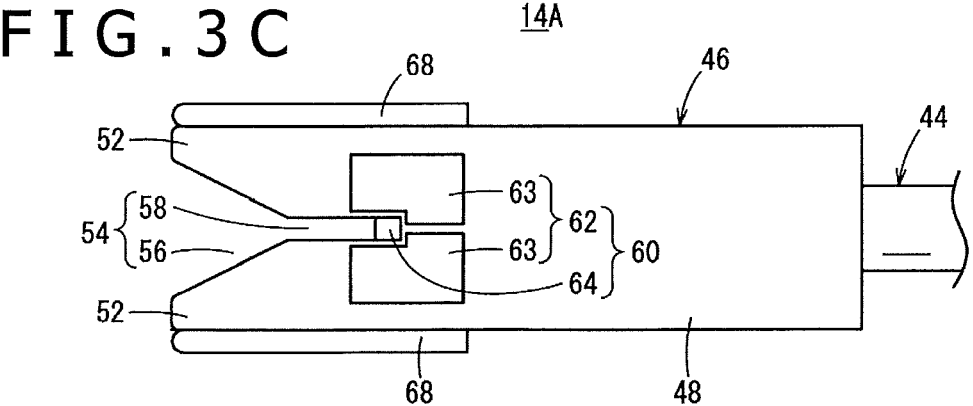
FIG. 3C is a bottom view of the distal portion of the second dissecting device.

As depicted in FIGS. 3B and 3C, the dissecting member 46 is provided with a treating section 60 for stanching and cutting the branch vessel 73. The treating section 60 includes a stanching section 62 for stanching the branch vessel 73, and a cutting section 64 (e.g., a cutting edge) for cutting the branch vessel 73. The stanching section 62 has a bipolar structure including a pair of electrodes 63. The pair of electrodes 63 are provided respectively on both sides of the second groove section 58 in the width direction. The pair of electrodes 63 are attached to a bottom surface of the dissecting member 46 as illustrated in FIG. 3C. The pair of electrodes 63 may be embedded in the dissecting member 46 in other embodiments.

Application of a high-frequency voltage between the pair of electrodes 63 thus configured permits a branch vessel 73 that has been guided into the second groove section 58 to be stanched by cauterization (thermal coagulation). This structure can also be used for stanching of blood vessels in area surrounding the branch vessel 73 that are not guided into the second groove section 58. The cutting section 64 is provided at a deepest part (i.e., proximal-most part) of the second groove section 58. The cutting section 64 is proximal to the distal ends of the pair of electrodes 63. This positional relationship ensures that the cauterized branch vessel 73 can be cut by the cutting section 64 (i.e., the branch vessel 73 is cauterized before being cut by the cutting section 64). When the cutting section 64 is an electrode, application of a high-frequency voltage between the cutting section 64 and the electrode 63 permits the branch vessel 73 guided into the second groove section 58 to be stanched by cauterization (thermal coagulation). These high-frequency voltages may be applied simultaneously or may be applied in a switching (alternating) manner by use of a switch.

The width of the second groove section 58 may be constant along the lengthwise direction of the second groove section 58 or may gradually decrease in the proximal direction (i.e., gradually decrease from the distal end of the second groove section 58 to the proximal end of the second groove section 58). The width of the second groove section 58 is preferably smaller than the outer diameter of the branch vessel 73. This makes it possible to press the branch vessel 73 flat within the second groove section 58 to reliably perform the cauterization at the stanching section 62.

The dissecting member 46 further includes a pair of guide plates 68 formed on both lateral sides (i.e., in the width direction) of the dissecting section 50 as illustrated in FIG. 1. Each of the guide plates 68 has an edge portion 69 (see FIG. 3B) which protrudes to the front side and the upper side as compared to the dissecting section 50 (i.e., the edge portion 69 protrudes distally beyond the dissecting section 50 and vertically beyond the dissecting section 50 in the thickness direction). A distal region of the edge portion 69 is inclined such as to be displaced upward in the proximal direction. The pair of guide plates 68 help ensure that when the second dissecting device 14A is pushed forward in the distal direction within a living body, the guide plates 68 are inserted into dissected parts precedingly formed by the side sections 24 of the dissecting member 18. Consequently, the second dissecting device 14A can be easily pushed forward along the blood vessel 72.

[Blood Vessel Harvesting Method]

A blood vessel harvesting method using the dissecting system 10 configured as described above will now be described. The blood vessel harvesting method includes a dissecting step (first step) of dissecting a blood vessel 72 in the state of the blood vessel 72 being covered with surrounding fat 74 (tissue) by use of the dissecting system 10, a cutting step (second step) of cutting the ligated blood vessel 72, and an extracting step (third step) of extracting the blood vessel 72 while the blood vessel 72 is covered with the surrounding fat 74 from the living body. In this example, the explanation will involve harvesting a saphenous vein in a lower limb.

Figure 4:
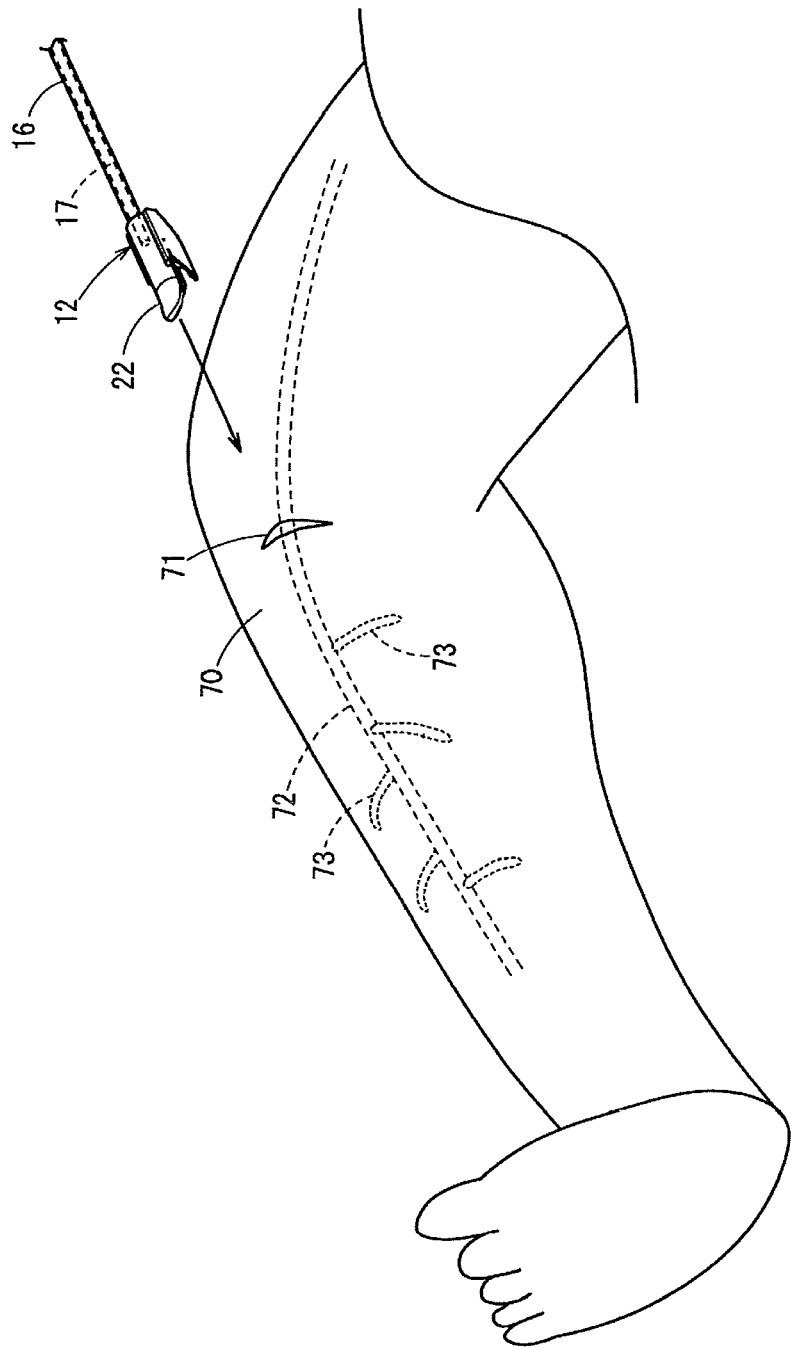
FIG. 4 illustrates a method of inserting the first dissecting device into a living body.

In the dissecting step, the position of the blood vessel 72 to be harvested is first confirmed. The patient's skin 70 is incised based on the position, as illustrated in FIG. 4, for example. After the skin 70 is incised to create an incision 71, the fat 74 is dissected until the blood vessel 72 appears (i.e., until the blood vessel 72 or a saphenous fascia is exposed). The first dissecting device 12 with the imaging device 17 inserted in the dissecting device 12 is then prepared. The first dissecting device 12 may instead be preliminarily provided with the imaging device 17 as a component of the first dissecting device 12.

While observing the inside of the living body through the imaging device 17, the first dissecting device 12 is then inserted into the living body along the blood vessel 72 via the incision 71. The first dissecting device 12 is inserted so that the base section 22 of the dissecting member 18 is disposed between the skin 70 and the blood vessel 72, and the thickness direction of the base section 22 coincides with the direction of alignment of the base section 22 with the blood vessel 72.

Figure 5:
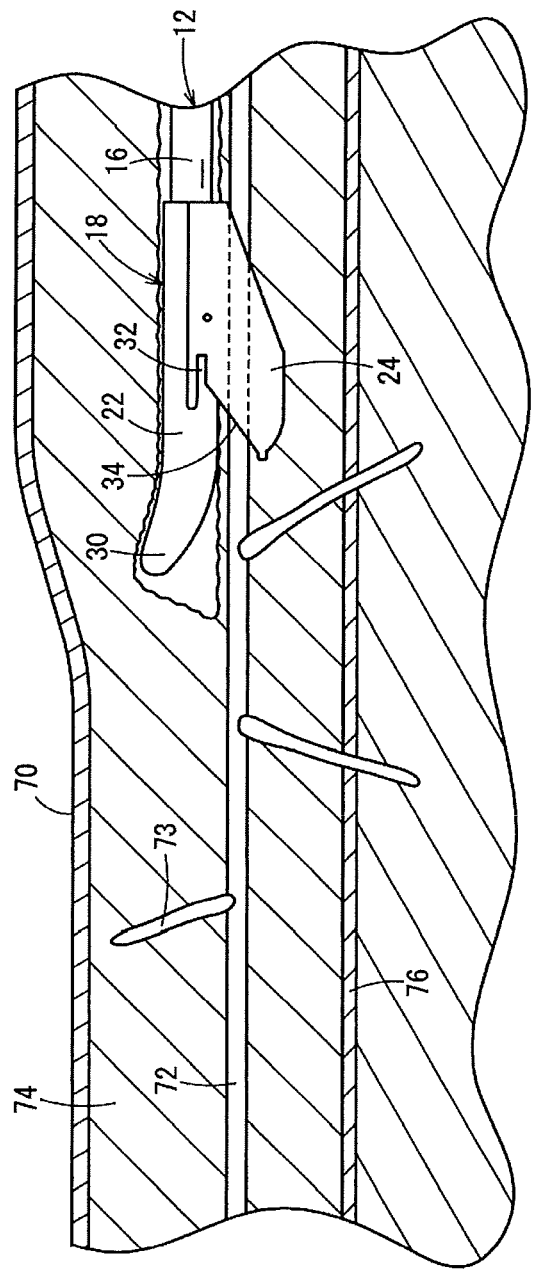
FIG. 5 is a sectional view along an extending direction of a blood vessel, illustrating a state in which the first dissecting device is pushed forward along the blood vessel in the living body.

The first dissecting device 12 is then pushed forward in the living body along the blood vessel 72 by a distance corresponding to a required length (e.g., a predetermined length to be harvested). As illustrated in FIG. 5, the first dissecting device 12 is moved forward while dissecting the fat 74 surrounding the blood vessel 72 with the dissecting member 18. More specifically, the distal dissecting section 30 of the base section 22 dissects the fat 74 present on the upper side (the skin 70 side) of the blood vessel 72 in the thickness direction of the base section 22 when the first dissecting device 12 moves forward.

Figure 6:
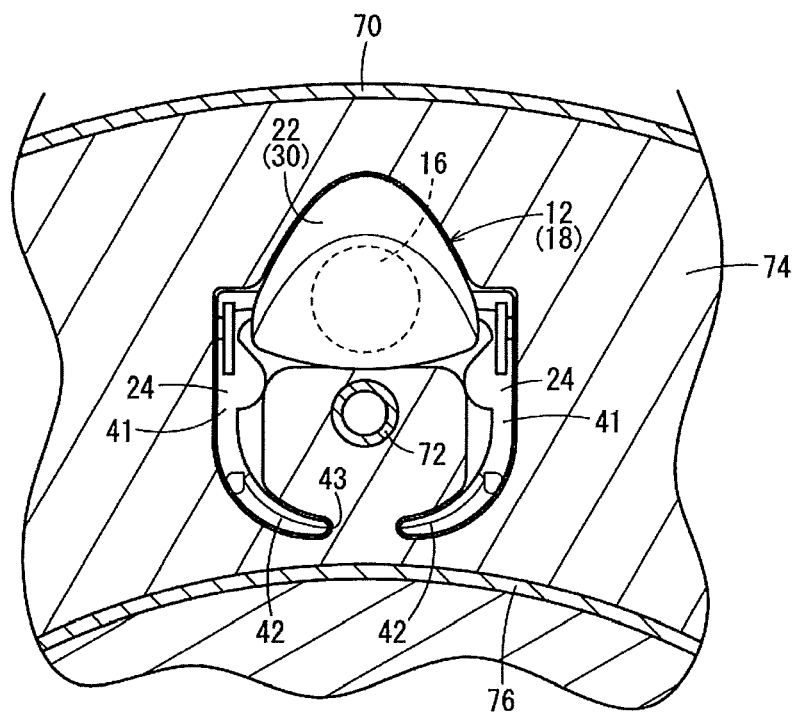
FIG. 6 is a sectional view in a direction perpendicular to the blood vessel, illustrating the state in which the first dissecting device is pushed forward along the blood vessel in the living body.

As shown in FIG. 6, the pair of side sections 24 dissect the fat 74 present on lateral sides in the width direction and the lower side (a fascia 76 side) of the blood vessel 72 in the thickness direction of the side sections 24. Specifically, the side wall portions 41 dissect the fat 74 on the lateral sides of the blood vessel 72 in the thickness direction of the side wall portions 41 (in the width direction of the base section 22). The projecting portions 42 additionally dissect the fat 74 present on the lower side (the fascia 76 side) of the blood vessel 72 (excluding a part in the space 43) in the thickness direction of the projecting portions 42.

When the first dissecting device 12 is moved forward within the living body along the blood vessel 72 as shown in FIG. 5, the first dissecting device 12 guides a branch vessel 73 (branched from the blood vessel 72) by the guide section 34 into the groove section 32. The treating section 36 provided at the groove section 32 of the first dissecting device 12 stanches and cuts the branch vessel 73 (see FIG. 2). A branch vessel 73 that comes into contact with the lower side of the projection-formed distal ends of the side sections 24 (at the time of contact of the dissecting member 18 with the branch vessel 73) is guided into the space 43 between the pair of projecting portions 42 and, therefore, is not subjected to stanching and cutting by the treating section 60.

After the first dissecting device 12 is moved forward by the distance corresponding to the required length (i.e., the predetermined length to be harvested of the blood vessel 72), the first dissecting device 12 is drawn out of (i.e., removed from) the living body via the incision 71 shown in FIG. 4.

The fat 74 present on the lower side (the fascia 76 side) of the blood vessel 72 exposed through the incision 71 is next dissected. The fat 74 is dissected by a technician's hand or by use of an appropriate device. Subsequently, the second dissecting device 14A (with the imaging device 17 inserted in the second dissecting device 14A) is inserted via the incision 71. The second dissecting device 14A is disposed in the fat 74 on the lower side of the blood vessel 72. The second dissecting device 14A may instead be preliminarily provided with the imaging device 17 as a component of the second dissecting device 14A.

Figure 7A:
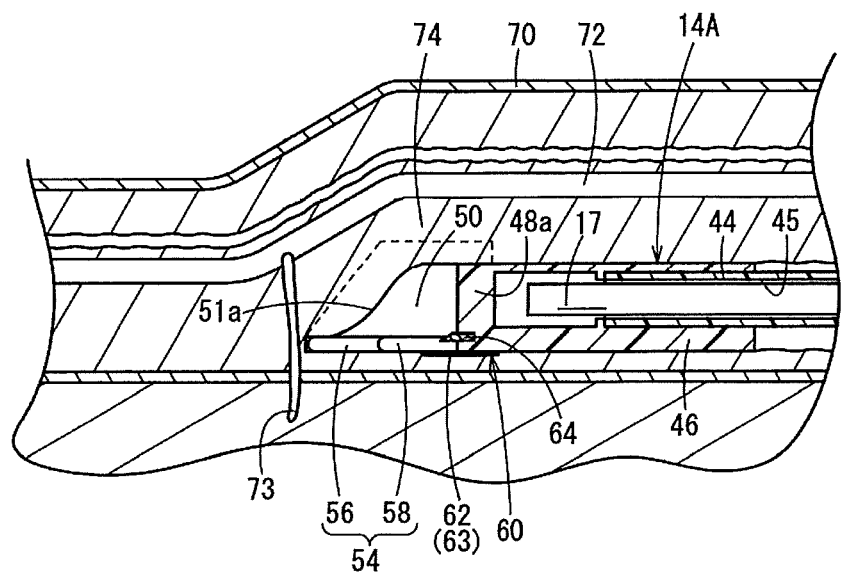
FIG. 7A is a sectional view along an extending direction of a blood vessel, illustrating a state in which the second dissecting device is pushed forward along the blood vessel in a living body.
Figure 8:
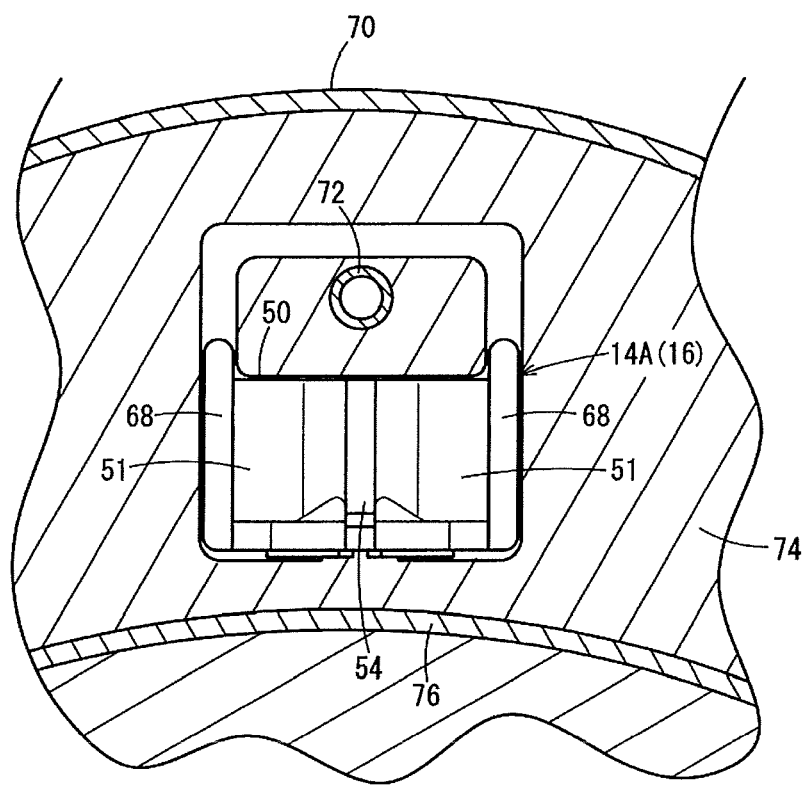
FIG. 8 is a sectional view in a direction perpendicular to the blood vessel, illustrating the state in which the second dissecting device is pushed forward along the blood vessel in the living body.

The second dissecting device 14A is then moved forward in the living body within the fat 74 along the blood vessel 72 by a distance corresponding to the required length (i.e., the predetermined length to be harvested). As depicted in FIG. 7A, when the second dissecting device 14A is moved forward in the fat 74 on the lower side of the blood vessel 72, the second dissecting device 14A dissects the fat 74 by the dissecting section 50 of the dissecting member 46 while forcing open the fat 74 and lifting the blood vessel 72 towards the upper side (the skin 70 side) along the inclined surface 51a of the dissecting section 50. As illustrated in FIG. 8, the dissecting section 50 lifts the blood vessel 72 towards the upper side (the skin 70 side) while the fat 74 on the lower side of the blood vessel 72 is being dissected by the dissecting section 50 from the fat 74 on the lower side of the second dissecting device 14A in the thickness direction of the dissecting member 46 (in the direction of alignment of the dissecting member 46 with the blood vessel 72). A dissected part is formed by this movement of the second dissecting device 14A to surround the whole circumference of the blood vessel 72. In other words, the fat 74 can be dissected in the whole circumferential range of the perimeter of the blood vessel 72.

Figure 7B:
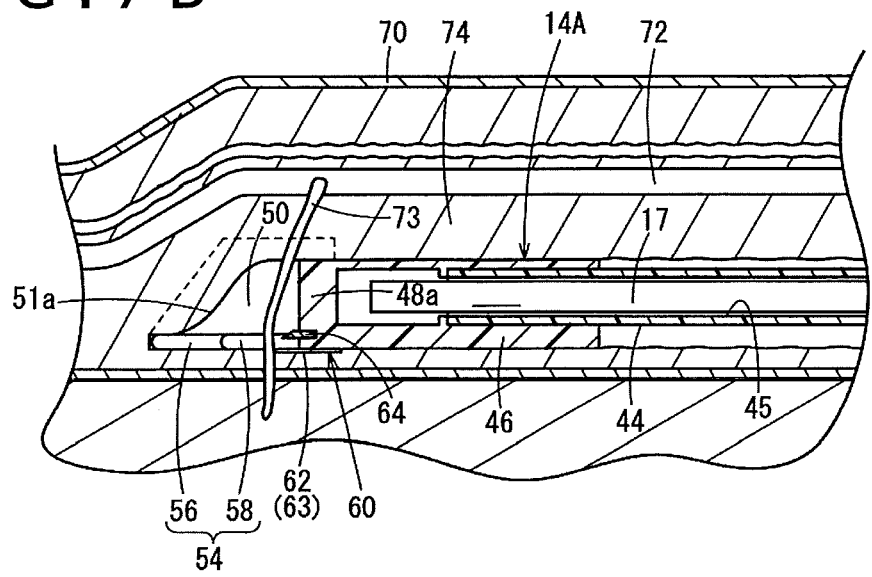
FIG. 7B is a sectional view of a state in which the second dissecting device has been further pushed forward.

When the second dissecting device 14A is moved forward within the living body along the blood vessel 72, the second dissecting device 14A is moved forward in the fat 74 on the lower side of the blood vessel 72 and dissects the fat 74 by the dissecting section 50 of the dissecting member 46 while forcing open the fat 74 and lifting the blood vessel 72 toward the upper side (the skin 70 side) along the inclined surface 51a of the dissecting section 50 as shown in FIG. 7B. The dissecting section 50 lifts the blood vessel 72 to the upper side (the skin 70 side) while the fat 74 on the lower side of the blood vessel 72 is being dissected by the dissecting section 50 from the fat 74 on the lower side of the second dissecting device 14A (i.e., in the thickness direction of the dissecting member 46 or in the direction of alignment of the dissecting member 46 with the blood vessel 72). The branch vessel 73 is thus stretched and exposed from the fat 74. The exposed branch vessel 73 is guided by the blood vessel guide passage 54 to the distal end wall 48a of the base part 48 and the treating section 60. The branch vessel 73 is brought into contact with the distal end wall 48a of the base part 48, and then the branch vessel 73 is stanched and cut by the treating section 60.

A branch vessel 73 that branches to the lower side (in the thickness direction) from the blood vessel 72 is drawn near (guided) by the first groove section 56 of the blood vessel guide passage 54. The branch vessel 73 is then guided by the second groove section 58 to the distal end wall 48a of the base part 48 and the treating section 60. The branch vessel 73 is brought into contact with the distal end wall 48a of the base part 48 (i.e., the branch vessel 73 is guided to the treating section 60), and the branch vessel 73 is stanched (cauterized) by the stanching section 62 and thereafter cut by the cutting section 64 of the treating section 60. The branch vessel 73 may be guided to the treating section 60 without making contact with the distal end wall 48a of the base part 48.

After the second dissecting device 14A is moved forward by a distance corresponding to the required length (i.e., the predetermined length to be harvested of the blood vessel 72), the second dissecting device 14A is drawn out of (removed from) the living body via the incision 71.

The dissecting step of dissecting the blood vessel 72 in the state of the blood vessel 72 being covered with the surrounding fat 74 (tissue) is completed by the above-described operations.

Since the dissecting member 46 of the second dissecting device 14A is provided with the blood vessel guide passage 54, it is possible for the user to dissect the tissue (the fat 74) in the living body and to easily capture the branch vessel 73 embedded in the tissue when inserting the second dissecting device 14A along the blood vessel 72. As a result, the user can easily stanch and cut the branch vessel 73 while observing the captured branch vessel 73 through the imaging device 17 inserted in the insertion lumen 45.

According to the second dissecting device 14A, the tissue surrounding the branch vessel 73 captured by the blood vessel guide passage 54 can be reduced in amount because the blood vessel guide passage 54 is thinner (smaller in diametric size) than the insertion lumen 45. The visibility of the branch vessel 73 through the imaging device 17 is thus enhanced, so that the user can easily perform the treatment of stanching and cutting the branch vessel 73. When the width of a proximal portion of the blood vessel guide passage 54 is narrower than the width of a distal portion of the blood vessel guide passage 54, the surrounding tissue can be more effectively dissected from the branch vessel 73.

The user can also easily guide the branch vessel 73 into the blood vessel guide passage 54 of the second dissecting device 14A because the distal portion of the blood vessel guide passage 54 is provided with the first groove section 56 (introducing section) having a width decreasing in the proximal direction.

The proximal portion of the blood vessel guide passage 54 includes the treating section 60 for stanching and cutting the branch vessel 73. This configuration of the second dissecting device 14A helps ensure that the user can capture the branch vessel 73 and stanch and cut the branch vessel 73 through a simple operation of moving the second dissecting device 14A forward and outputting energy to the treating section 60. Note that the treating section 60 may not necessarily be provided with the cutting section 64. In that case, the user may cut the branch vessel 73 stanched with the stanching section 62 by using an appropriate cutting device separate from the second dissecting device 14A.

The tissue in the living body can be effectively dissected by the second dissecting device 14A because the thickness of the dissecting section 50 gradually increases in the proximal direction (i.e., from the distal end to the proximal end).

Figure 9A:
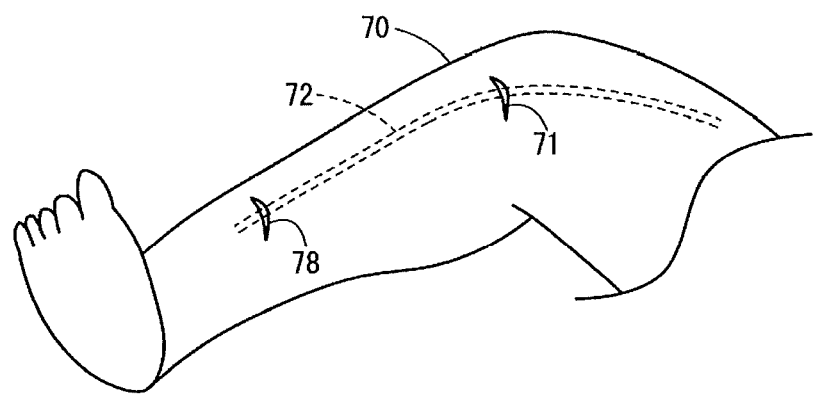
FIG. 9A illustrates cutting of a blood vessel to be harvested.

When the dissecting step is complete, the cutting step is conducted next. As depicted in FIG. 9A, the cutting step includes incising the skin 70 at a position spaced from the incision 71 to create an incision 78. The incision 78 is spaced from the incision 71 by a distance corresponding to the length of the blood vessel 72 to be harvested, whereby the blood vessel 72 is exposed at the incision 78. Both ends of that part of the blood vessel 72 which is to be harvested are ligated by way of the two incisions 71 and 78, after which the blood vessel 72 is cut.

Figure 9B:
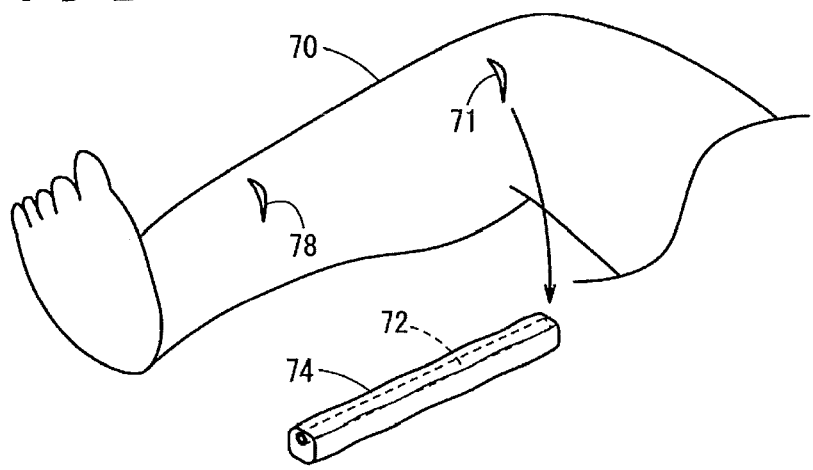
FIG. 9B illustrates extraction of the blood vessel accompanied with fat from the inside of the living body.

The extracting step is performed after the cutting step is complete. In the extracting step, the blood vessel 72 accompanied with the fat 74 is extracted to the outside of the living body through the incision 71 or the incision 78 as shown in FIG. 9B.

The blood vessel 72 accompanied with the fat 74 can be harvested from the living body by performing the dissecting, cutting and extracting described above. The blood vessel 72 can be harvested smoothly and with low invasion by this method. It is possible to let blood flow in the blood vessel 72 for a prolonged time because the dissecting can be carried out without cutting the blood vessel 72. Consequently, the blood vessel 72 kept in an ischemic state for a shorter time and accompanied with less damage can be harvested.

A blood vessel 72 covered with the fat 74 is characterized in that lowering of blood flow due to expansion or bending can be inhibited, damage to endotheliocyte, smooth muscle, nutrient vessels (a network of small blood vessels) and the like can be reduced, and thickening of the blood vessel wall can be suppressed. Using a blood vessel 72 covered with the fat 74 as a bypass vessel thus offers an excellent long-term patency rate. Since the blood vessel 72 accompanied with the fat 74 thus harvested has nutrient vessels remaining in the blood vessel wall or the fat 74, it is considered that nutrients are supplied to the blood vessel 72 serving as the bypass vessel after bypass grafting, so that the above-mentioned effects are enhanced.

Although the user harvests the blood vessel 72 accompanied with the fat 74 by using the first dissecting device 12 and the second dissecting device 14A in the above description, the blood vessel 72 accompanied with the fat 74 may be harvested by using only the second dissecting device 14A without using the first dissecting device 12. In this case, the above-described operation of inserting and moving the second dissecting device 14A forward is repeated a plurality of times (more than once), whereby the fat 74 can be dissected over the whole circumferential range of the perimeter of the blood vessel 72. The projections 52 provided at the distal ends of the dissecting section 50 serve as starting points of dissection of the fat 74 in the living body. The fat 74 can accordingly be dissected easily.

The order in which the first dissecting device 12 and the second dissecting device 14A are inserted into the living body may be reversed from that in the above description. For example, the second dissecting device 14A may first be inserted into the living body and moved forward along the blood vessel 72, then the second dissecting device 14A may be drawn out of the living body, and thereafter the first dissecting device 12 can be inserted into the living body and moved forward along the blood vessel 72.

The second incision 78 may be formed simultaneously with the first incision 71. Alternatively, the second incision 78 may be formed after the first device (the first dissecting device 12, when the first dissecting device 12 and the second dissecting device 14A are used in that order) is inserted into the living body (in the period until the insertion of the second one of the two dissecting devices into the living body).

The first device may be taken out via the second incision 78. The second device (the second dissecting device 14A, when the first dissecting device 12 and the second dissecting device 14A are used in that order) may be inserted by way of the second incision 78.

In the dissecting system 10 and the blood vessel harvesting method described above, dissecting devices 14B and 14C (hereinafter referred to as "the second dissecting device 14B" and "the second dissecting device 14C," respectively) shown in FIGS. 10 to 17B may be utilized in place of the second dissecting device 14A. Alternatively, the above-described dissecting step may be carried out by using only the second dissecting device 14B or only the second dissecting device 14C. The same or equivalent components of the second dissecting device 14B or the second dissecting device 14C to those of the second dissecting device 14A described above are denoted by the same reference symbols as used above. Overlapping component descriptions will be omitted.

[Second Dissecting Device 14B]

Figure 10:
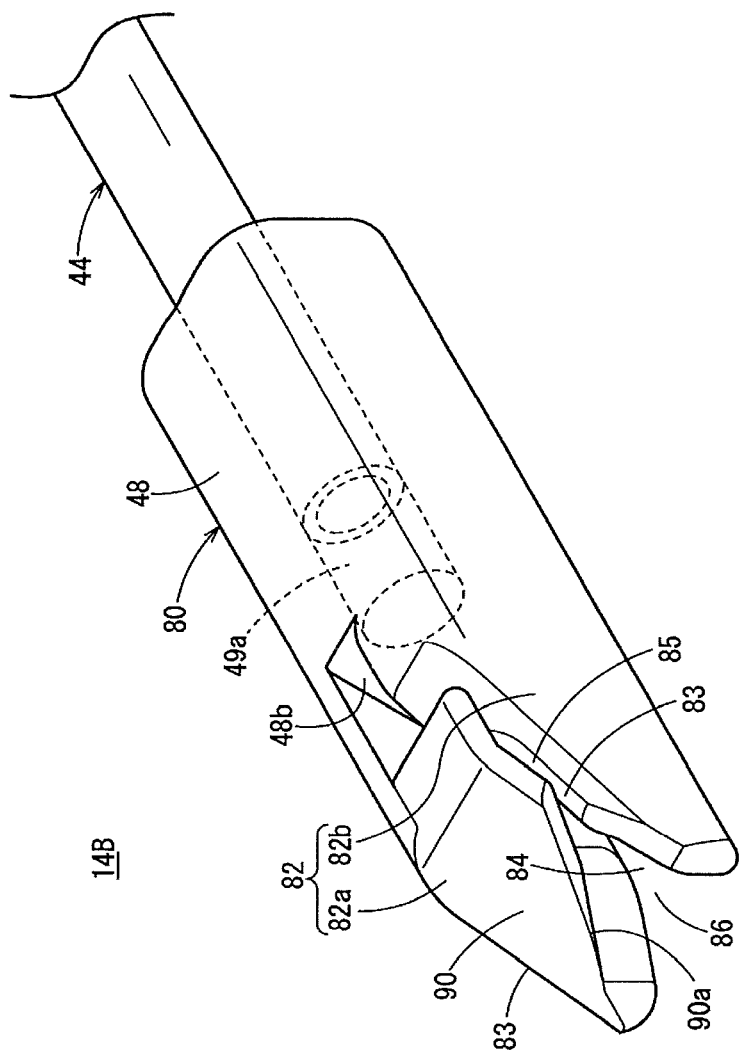
FIG. 10 is a perspective view of a distal portion of a second dissecting device according to another embodiment.

The second dissecting device 14B shown in FIG. 10 is an elongated device to be inserted (i.e., insertable) into a living body along a blood vessel 72, such as a saphenous vein. The second dissecting device 14B includes a grasping section 44 adapted (configured) to be graspable by the user and a dissecting member 80 at a distal portion of the grasping section 44. The grasping section 44 of the second dissecting device 14B is configured in the same manner as the grasping section 44 of the second dissecting device 14A.

The dissecting member 80 includes a base part 48 fixed to a distal portion of the grasping section 44, a dissecting section 82 extending distally from the distal end of the base part 48, a blood vessel guide passage 84 in the dissecting section 82, and a roof section 90 in the dissecting section 82. The base part 48 of the dissecting member 80 is configured in the same manner as the base part 48 of the dissecting member 46 illustrated in FIG. 1 and the like, except that the base part 48 of the dissecting member has an inclined front surface wall (an inclined surface 48b).

Figure 11A:
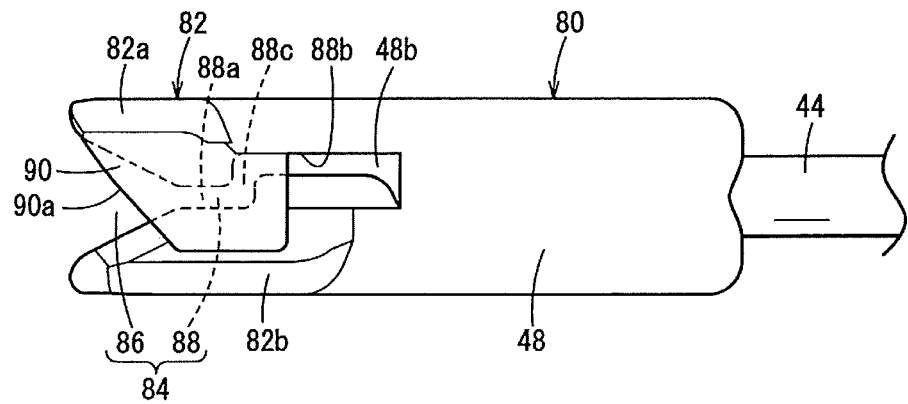
FIG. 11A is a plan view of the distal portion of the second dissecting device shown in FIG. 10.
Figure 11B:
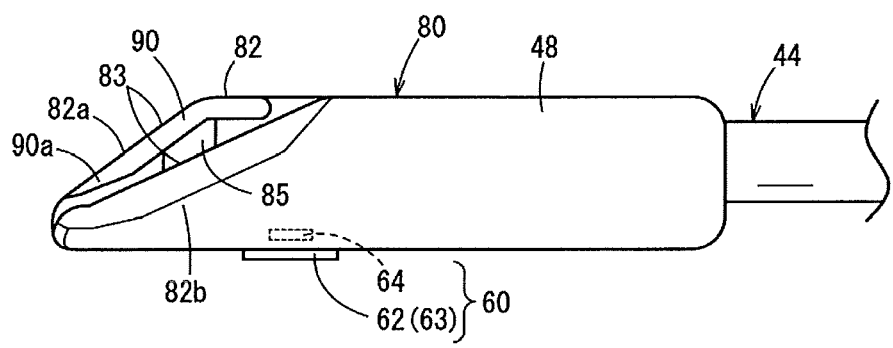
FIG. 11B is a side view of the distal portion of the second dissecting device shown in FIG. 10.

The dissecting section 82 includes a pair of dissecting portions 82a and 82b which dissect tissue (fat 74 or the like) when the dissecting member 80 is moved forward along the blood vessel 72. The pair of dissecting portions 82a and 82b are spaced apart from each other in the width direction of the dissecting member 80. "The width direction of the dissecting member 80" means a direction perpendicular to the axial direction (longitudinal direction) of the dissecting device 14B and perpendicular to the thickness direction of the dissecting member 80 (the direction of dissection of the fat 74 by the dissecting member 80; the vertical direction in FIG. 11B). For easy dissection of tissue in the direction of alignment of the blood vessel 72 with the dissecting member 80, the thickness (the dimension measured in the height direction of the dissecting member 80) of the dissecting section 82 gradually increases in the proximal direction. Specifically, each of the dissecting portions 82a and 82b has an inclined surface 83 inclined such as to be displaced upward in the proximal direction. In other words, each inclined surface 83 is gradually inclined between a distal-most lower edge to a proximal-most upper edge as illustrated in FIGS. 10 and 11B.

Figure 11C:
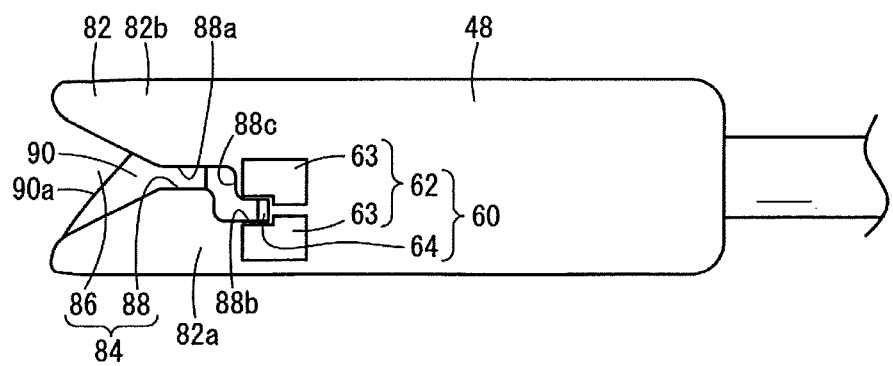
FIG. 11C is a bottom view of the distal portion of the second dissecting device shown in FIG. 10.

The blood vessel guide passage 84 is provided in a distal portion of the dissecting member 80. The blood vessel guide passage 84 accepts a branch vessel 73 from the distal side of the dissecting member 80 and guides the branch vessel 73 to the base part 48 side. The blood vessel guide passage 84 is formed between the above-mentioned pair of dissecting portions 82a and 82b. As depicted in FIGS. 11A and 11C, the blood vessel guide passage 84 includes a first groove section 86 (introducing section) constituting a distal-side region of the blood vessel guide passage 84 and a second groove section 88 constituting a proximal-side region of the blood vessel guide passage 84. The width of the first groove section 86 decreases in the proximal direction.

The second groove section 88 communicates with the first groove section 86. The second groove section 88 has a smaller width than the first groove section 86. The width of the second groove section 88 may be constant along the lengthwise direction of the second groove section 88 or may gradually decrease in the proximal direction (i.e., from the distal end of the second groove section 88 to the proximal end of the second groove section 88). The width of the second groove section 88 is preferably smaller than the outer diameter of the branch vessel 73. This makes it possible to press the branch vessel 73 flat within the second groove section 88 to reliably perform cauterization at a stanching section 62. This configuration also helps ensure that the fat 74 surrounding the branch vessel 73 can be separated more effectively.

The second groove section 88 possesses a crooked shape (e.g., a crank shape or a bent shape). The second groove section 88 includes a first guide passage 88a constituting a distal-side region, a second guide passage 88b constituting a proximal-side region, and an intermediate guide passage 88c constituting an intermediate region.

The first guide passage 88a extends proximally from a proximal end of the first groove section 86 and extends rectilinearly in the longitudinal direction of the dissecting member 80. The second guide passage 88b communicates with the first guide passage 88a through the intermediate guide passage 88c. The second guide passage 88b extends rectilinearly in the longitudinal direction of the dissecting member 80. The center axis of the second guide passage 88b is located at a position deviated from the position of the center axis of the first guide passage 88a in the width direction of the dissecting member 80 (the width direction of the first guide passage 88a). The intermediate guide passage 88c extends in a direction intersecting the first guide passage 88a and the second guide passage 88b (in the illustrated example, in a direction orthogonal/perpendicular to the first guide passage 88a and the second guide passage 88b). This configuration helps enable the fat 74 surrounding the branch vessel 73 to be separated more effectively. The first guide passage 88a and the second guide passage 88b may communicate directly with each other in some embodiments. In that case, a proximal portion of the first guide passage 88a and a distal portion of the second guide passage 88b form a certain angle relative to one another. The certain angle is greater than 90 degrees and smaller than 180 degrees. This enables a further effective separation of the fat 74 surrounding the branch vessel 73. The width of the second guide passage 88b may be smaller than the width of the first guide passage 88a. This enables the fat 74 surrounding the branch vessel 73 to be separated more effectively.

The dissecting member 80 includes a treating section 60 for stanching and cutting the branch vessel 73 on the proximal side of the second groove section 88 as illustrated in FIGS. 11B and 11C. The treating section 60 of the dissecting member 80 is configured in the same manner as the treating section 60 of the dissecting member 46.

The roof section 90 is configured to cover the blood vessel guide passage 84 and the dissecting section 82 at least partly as illustrated in FIG. 10. The roof section 90 permits the branch vessel 73 to pass between the roof section 90 and the dissecting section 82. The roof section 90 is formed at the inclined surface 83 of the dissecting portion 82a on one side and projects from the dissecting portion 82a on the one side toward the dissecting portion 82b on the other side to partly cover the blood vessel guide passage 84. A projecting end portion of the roof section 90 partly covers the inclined surface 83 of the dissecting portion 82b on the other side.

The roof section 90 configured is this manner helps ensure that the fat 74 surrounding the branch vessel 73 can be separated (scraped off) when the branch vessel 73 is guided into the blood vessel guide passage 84. In the dissecting member 80 in the example illustrated in FIG. 10, a space 85 is formed between the roof section 90 and the dissecting section 82. It is preferable that the space 85 (e.g., the distance between the inner surface of the roof section 90 and the inclined surface 83) is roughly equal to or smaller than the outer diameter of the branch vessel 73. This enables the fat 74 surrounding the branch vessel 73 to be separated more effectively.

The roof section 90 may be configured to be elastically deformable to move away (space apart or separate) from the dissecting section 82 when a force is exerted thereon upon making contact with the branch vessel 73. The roof section 90 and the dissecting section 82 may be in contact with each other in an initial state. In this case, although no space is formed between the roof section 90 and the dissecting section 82 in the initial state, a space is formed between the roof section 90 and the dissecting section 82 due to elastic deformation of the roof section 90 upon contact between the roof section 90 and the branch vessel 73. The space 85 that is formed in this manner allows the branch vessel 73 to pass between the roof section 90 and the dissecting section 82.

An inclined edge portion 90a is at a distal portion of the roof section 90 as illustrated in FIGS. 10, 11A, and 11C. The inclined edge portion 90a of the roof section 90 is inclined from the side of the dissecting portion 82a on one side toward the side of the projecting end of the roof section 90 in the proximal direction. In other words, the inclined edge portion 90a extends between a distal-most end at an outside of the dissecting portion 82a in the width direction to a proximal-most end at the outside of the opposite side of the roof section 90 in the width direction as illustrated in FIG. 11A. This inclined edge portion 90a enables the branch vessel 73 to be smoothly guided into the space 85 between the roof section 90 and the dissecting section 82 upon the contact of the branch vessel 73 with the roof section 90.

When the first dissecting device 12 shown in FIG. 1 and the second dissecting device 14B illustrated in FIG. 10 are used together, the blood vessel 72 to be used as a bypass vessel can be harvested by performing the dissecting step, the cutting step and the extracting step in the same manner as described above.

Figure 12:
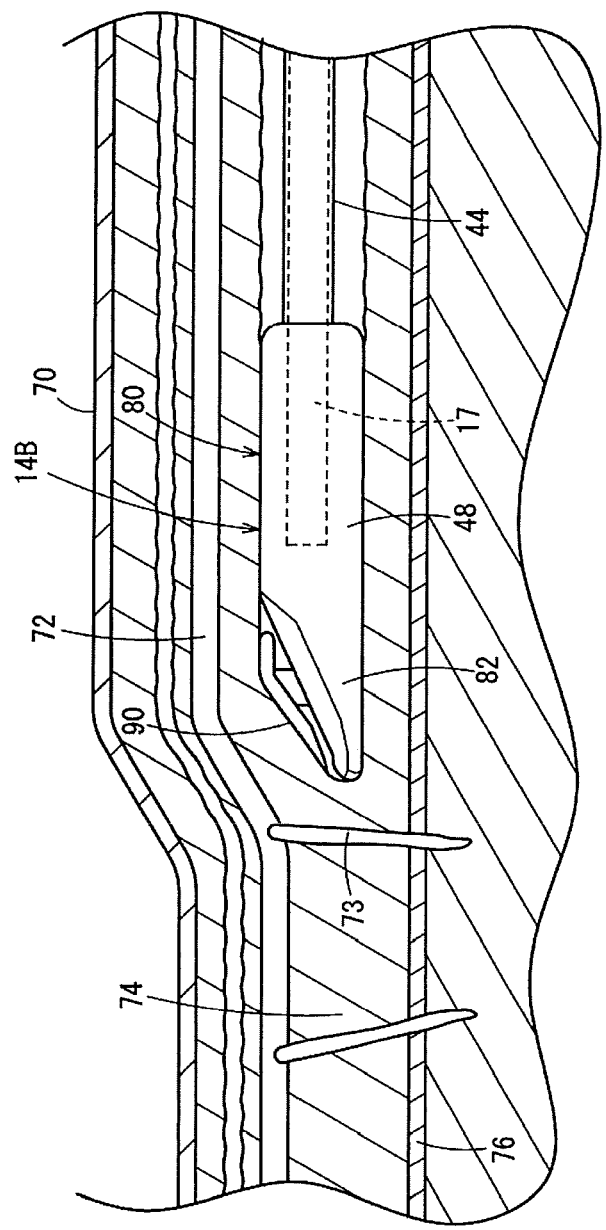
FIG. 12 is a sectional view along an extending direction of a blood vessel, illustrating a state in which the second dissecting device shown in FIG. 10 is pushed forward along the blood vessel in a living body.

In the dissecting step conducted using the second dissecting device 14B, the dissecting member 80 dissects the fat 74 on the lower side of the blood vessel 72 in the thickness direction of the dissecting member 80 (in the direction of alignment of the dissecting member 80 with the blood vessel 72) with the dissecting section 82 when the second dissecting device 14B is moved forward in the living body along the blood vessel 72 as illustrated in FIG. 12. The second dissecting device 14B guides the branch vessel 73 to the treating section 60 (see FIG. 11B) by the blood vessel guide passage 84, and stanches and cuts the branch vessel 73 by the treating section 60.

The second dissecting device 14B draws in the branch vessel 73 by the first groove section 86 of the blood vessel guide passage 84. The second dissecting device 14B guides the branch vessel 73 to the treating section 60 by the second groove section 88. The first guide passage 88a accepts the branch vessel 73 from the first groove section 86 and guides the branch vessel 73 proximally into the intermediate guide passage 88c. The intermediate guide passage 88c accepts the branch vessel 73 from the first guide passage 88a and guides the branch vessel 73 into the second guide passage 88b that deviates (is spaced apart) from the first guide passage 88a in the width direction of the dissecting member 80. The second guide passage 88b accepts the branch vessel 73 from the intermediate guide passage 88c and guides the branch vessel 73 to the treating section 60. This configuration of guide passages makes it possible to separate the fat 74 surrounding the branch vessel 73 more effectively and to reliably treat the branch vessel 73.

Figure 13A:
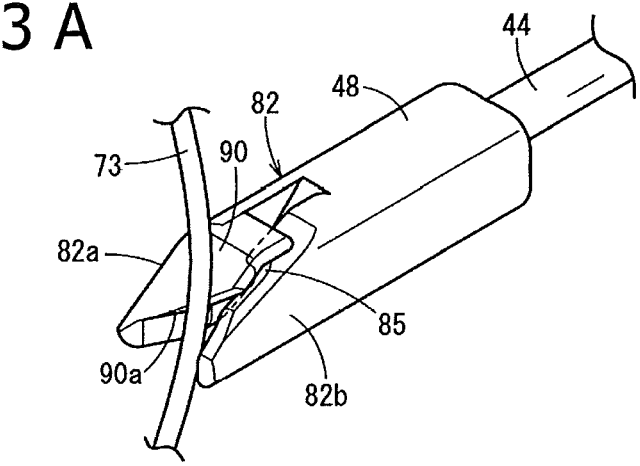
FIG. 13A is a first view illustrating capture of a branch vessel by the second dissecting device shown in FIG. 10.
Figure 13B:
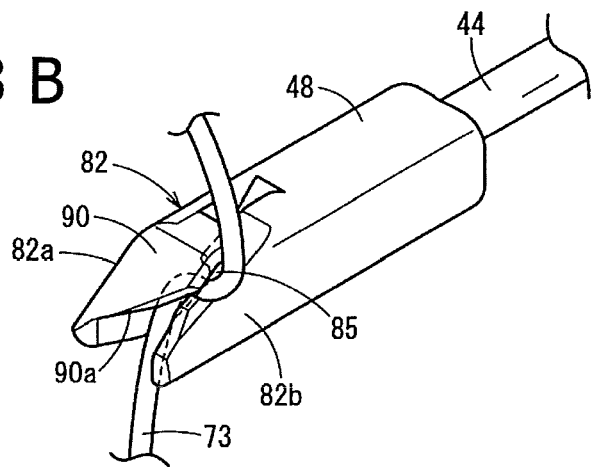
FIG. 13B is a second view illustrating the capture of the branch vessel by the second dissecting device shown in FIG. 10.
Figure 13C:
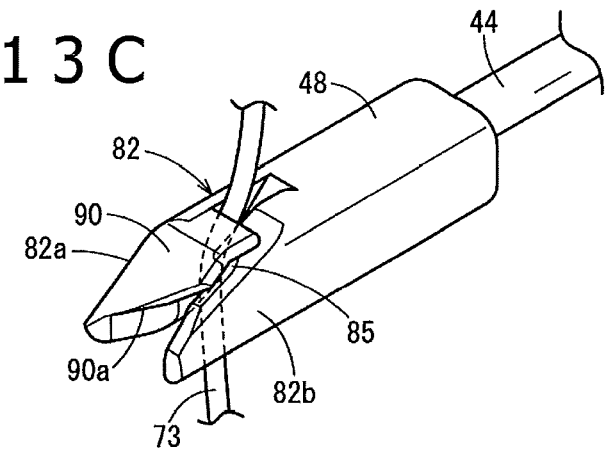
FIG. 13C is a third view illustrating the capture of the branch vessel by the second dissecting device shown in FIG. 10.

On the other hand, when the branch vessel 73 enters into the blood vessel guide passage 84 when the second dissecting device 14B is moved forward as shown in FIG. 13A, the branch vessel 73 is dissected while forcing open the fat 74 on the lower side of the blood vessel 72 and moving in the fat 74, under the guiding action of the inclined edge portion 90a of the roof section 90, and is smoothly guided toward the side of the projecting end of the roof section 90. Then, after further forward movement of the second dissecting device 14B, the branch vessel 73 enters into the space 85 between the roof section 90 and the dissecting section 82 while being twisted as depicted in FIG. 13B. After entering into the space 85, the branch vessel 73 moves within the space 85 toward the dissecting section 82 side. The branch vessel 73 thus reaches the blood vessel guide passage 84 while returning from the once twisted state into a rectilinear state, as shown in FIG. 13C.

The branch vessel 73 is then guided to the treating section 60 by the blood vessel guide passage 84 to be stanched (cauterized) by the stanching section 62 and thereafter cut by a cutting section 64.

The dissecting member 80 of the second dissecting device 14B includes the blood vessel guide passage 84 configured such that when the second dissecting device 14B is inserted along the blood vessel 72, the second dissecting device 14B can dissect the tissue (the fat 74) in the living body and can easily capture the branch vessel 73 embedded in the tissue. This ensures that the branch vessel 73 captured can be easily stanched and cut while an operator observes the branch vessel 73 through an imaging device 17 inserted in an insertion lumen 45.

The tissue surrounding the branch vessel 73 can be separated by the roof section 90 of the second dissecting device 14B when the branch vessel 73 is guided by the blood vessel guide passage 84. The tissue can thus be prevented or restrained from entering into a proximal portion (the treating section 60) of the blood vessel guide passage 84. This enhances visibility of the branch vessel 73, whereby the stanching and cutting operation for the branch vessel 73 can be carried out more effectively. The branch vessel 73 can also be smoothly guided to the proximal portion of the blood vessel guide passage 84 while the tissue surrounding the branch vessel 73 is dissected because the space 85 is formed between the roof section 90 and the dissecting section 82.

The blood vessel guide passage 84 of the second dissecting device 14B includes the first guide passage 88a, the second guide passage 88b, and the intermediate guide passage 88c. These three passages 88a, 88b and 88c form a crank-shaped crooked path. The surrounding tissue can thus be effectively dissected from the branch vessel 73 when the branch vessel 73 is guided by the blood vessel guide passage 84. The blood vessel guide passage 54 of the dissecting member 46 depicted in FIG. 3A and other embodiments of the dissecting device may include the same first guide passage 88a, the second guide passage 88b and the intermediate guide passage 88c as those of the blood vessel guide passage 84. The first guide passage 88a and the second guide passage 88b may communicate directly with each other. In that case, a proximal portion of the first guide passage 88a and a distal portion of the second guide passage 88b form a certain angle relative to one another. The certain angle is greater than 90 degrees and smaller than 180 degrees. This makes it possible to more effectively separate the fat 74 surrounding the branch vessel 73 and to reliably treat the branch vessel 73. The width of the second guide passage 88b is smaller than the width of the first guide passage 88a. This helps enable more effective separation of the fat 74 surrounding the branch vessel 73.

Those other parts of the second dissecting device 14B which are configured in the same manner as in the second dissecting device 14A produce the same advantageous effects as those of the corresponding parts of the second dissecting device 14A.

[Second Dissecting Device 14C]

Figure 14:
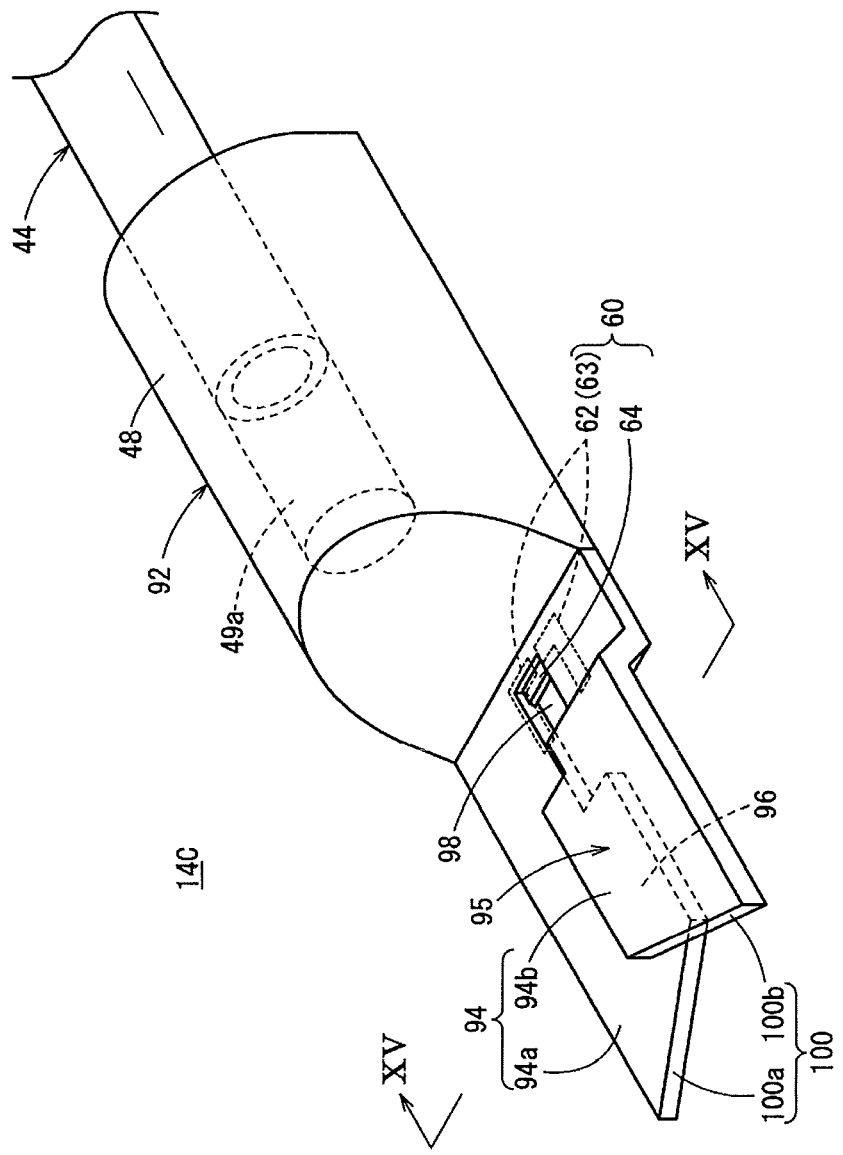
FIG. 14 is a perspective view of a distal portion of a second dissecting device according to another embodiment.

The second dissecting device 14C illustrated in FIG. 14 is an elongated device to be inserted (insertable) into a living body along a blood vessel 72 such as a saphenous vein. The second dissecting device 14C includes a grasping section 44 adapted (configured) to be graspable by the user and a dissecting member 92 at a distal portion of the grasping section 44. The grasping section 44 of the second dissecting device 14C is configured in the same manner as the grasping section 44 of the second dissecting device 14A.

The dissecting member 92 includes a base part 48 fixed to a distal portion of the grasping section 44 and a dissecting section 94 extending distally from the distal end of the base part 48. The base part 48 of the dissecting member 92 is configured in the same manner as the base part 48 of the dissecting member 46. The dissecting section 94 includes a pair of dissecting portions 94a and 94b which dissect tissue (fat 74 or the like) when the dissecting member 92 is moved forward along the blood vessel 72. The pair of dissecting portions 94a and 94b are both formed in a plate-like shape (i.e., plate-shaped) and are spaced apart from each other in the thickness direction of the dissecting member 92.

The pair of dissecting portions 94a and 94b overlap, at least partly, with each other in a width direction perpendicular to a longitudinal direction of the dissecting member 92. Specifically, the pair of dissecting portions 94a and 94b overlap partly with each other in plan view. An overlapping part 95 of the pair of dissecting portions 94a and 94b is configured to permit passage of a branch vessel 73 therethrough.

Figure 15:
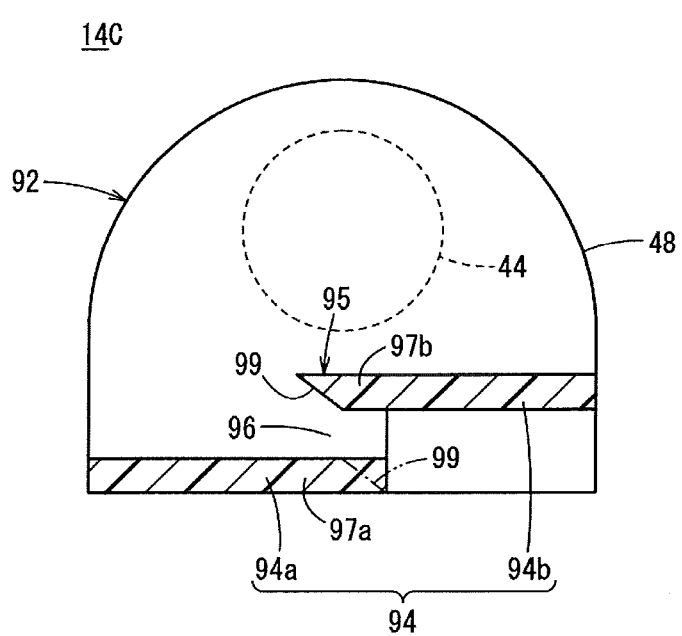
FIG. 15 is a sectional view taken along line XV-XV of FIG. 14.

As depicted in FIG. 15, a space 96 is between the pair of dissecting portions 94a and 94b in the thickness direction of the dissecting section 94. It is preferable that the space 96 is roughly equal to or smaller than the outside diameter of the branch vessel 73. This enables the fat 74 surrounding the branch vessel 73 to be separated effectively.

The pair of dissecting portions 94a and 94b have a pair of projecting portions 97a and 97b projecting toward each other. The overlapping part 95 is at the pair of projecting portions 97a and 97b. A groove section 98 which penetrates the dissecting section 94 in the thickness direction of the dissecting section 94 is proximal to the overlapping part 95. The groove section 98 is disposed on the front side of (distal to) the base part 48.

Only one of the pair of dissecting portions 94a and 94b may be provided with the projecting portion (the projecting portion 97a or the projecting portion 97b). The groove section 98 may have the same crooked shape or a similar shape to of the crooked shape of the second groove section 88 (that includes the first guide passage 88a, the second guide passage 88b and the intermediate guide passage 88c) of the dissecting member 80 shown in FIG. 11A and the like. This configuration helps enable more effective separation of the fat 74 surrounding the branch vessel 73. In another embodiment, the first guide passage 88a and the second guide passage 88b may communicate directly with each other. In that case, a proximal portion of the first guide passage 88a and a distal portion of the second guide passage 88b form a certain angle relative to one another (i.e., the first guide passage 88a extends away from the second guide passage 88b at an angle relative to the second guide passage 88b). The certain angle is greater than 90 degrees and smaller than 180 degrees. This enables a further effective separation of the fat 74 surrounding the branch vessel 73. The width of the second guide passage 88b is smaller than the width of the first guide passage 88a. This enables the fat 74 surrounding the branch vessel 73 to be separated more effectively.

At least one of the pair of dissecting portions 94a and 94b may be configured to be elastically deformable in the thickness direction when the branch vessel 73 contacts the dissecting portion 94a or 94b and exerts a force on the dissecting portion 94a or 94b. The pair of dissecting portions 94a and 94b may be in contact with each other in an initial state. In this case, a space 96 is created between the pair of dissecting portions 94a and 94b through elastic deformation of at least one of the pair of dissecting portions 94a and 94b when the pair of dissecting portions 94a and 94b are brought into contact with the branch vessel 73 even though a space 96 is not formed between the pair of dissecting portions 94a and 94b in the initial state. Therefore, the branch vessel 73 can pass between the pair of dissecting portions 94a and 94b. At least one of the pair of dissecting portions 94a and 94b (in FIG. 15, the dissecting portion 94b) is provided with an inclined surface 99 inclined at an acute angle relative to the longitudinal direction of the dissecting portions 94a and 94b when viewed in cross section as shown in FIG. 15. The inclined surface 99 is on the space 96 side of its end portion at the overlapping part 95 (i.e., towards the center in the width direction as shown in FIG. 15). It is thus easy for the branch vessel 73 to enter between the pair of dissecting portions 94a and 94b. The dissecting portion 94a may additionally be provided with an inclined surface 99 inclined at an acute angle on the space 96 side of its end portion at the overlapping part 95, as indicated by an imaginary line in FIG. 15. In another embodiment, only the end portion of the dissecting portion 94a at the overlapping part 95 may be provided with the inclined surface 99.

An introducing section 100 is at a distal portion of the dissecting section 94. The width of the introducing section 100 decreases in the proximal direction. Specifically, the introducing section 100 includes a first inclined end edge 100a provided at a distal portion of the dissecting portion 94a on one side to approach the dissecting portion 94b on the other side in the proximal direction, and a second inclined end edge 100b provided at a distal portion of the dissecting portion 94b on the other side to approach the dissecting portion 94a on the one side in the proximal direction. In other words, the first inclined end edge 100a and the second inclined edge 100b are gradually closer to one another from the distal end to the proximal end.

The dissecting member 92 includes a treating section 60 for stanching and cutting a branch vessel 73. The treating section 60 of the dissecting member 92 is configured in the same manner as the treating section 60 of the dissecting member 80 illustrated in FIGS. 11B and 11C.

When the first dissecting device 12 shown in FIG. 1 and the second dissecting device 14C configured as just-mentioned are used together, a blood vessel 72 to be used as a bypass vessel can be harvested by performing the dissecting step, the cutting step and the extracting step in the same manner as described above.

Figure 16:
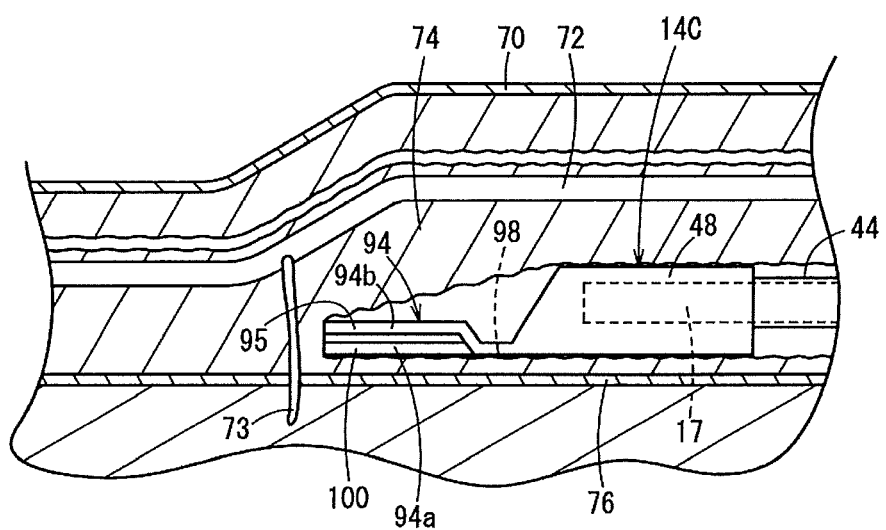
FIG. 16 is a sectional view along an extending direction of a blood vessel, illustrating a state in which the second dissecting device shown in FIG. 14 is pushed forward along the blood vessel in a living body.

In the dissecting step conducted using the second dissecting device 14C, the dissecting member 92 dissects the fat 74 on the lower side of the blood vessel 72 in the thickness direction of the dissecting member 92 (in the direction of alignment of the dissecting member 92 with the blood vessel 72) by the dissecting section 94 when the dissecting member 92 is moved forward within the living body along the blood vessel 72 as shown in FIG. 16. The second dissecting device 14C guides the branch vessel 73 to the treating section 60 (see FIG. 14) by the blood vessel guide passage 54, and stanches and cuts the branch vessel 73 by the treating section 60.

The second dissecting device 14C draws in the branch vessel 73 by the introducing section 100 when the second dissecting device 14C is advanced/moved forward within the living body. The second dissecting device 14C guides the branch vessel 73 to the treating section 60 through the overlapping part 95 of the pair of dissecting portions 94a and 94b. The branch vessel 73 is smoothly guided to the overlapping part 95 by a guiding action of the introducing section 100 (the first inclined end edge 100a and the second inclined end edge 100b).

Figure 17A:
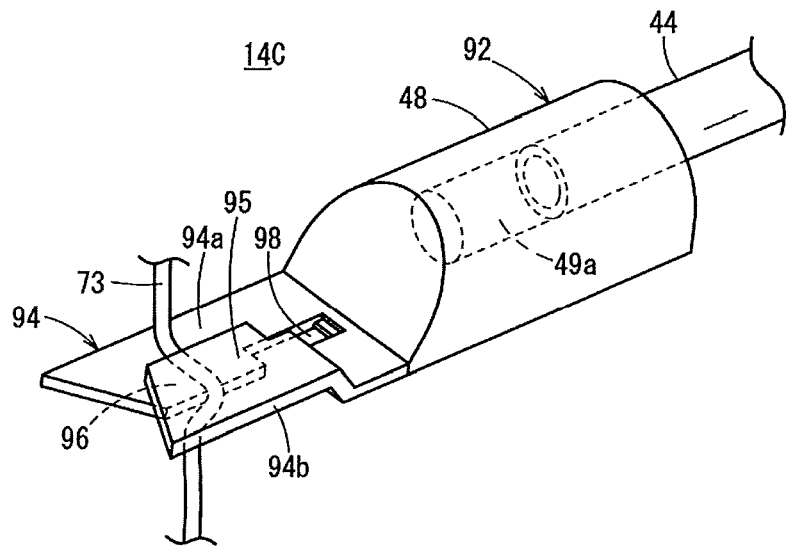
FIG. 17A is a first view for illustrating capture of a branch vessel by the second dissecting device shown in FIG. 14.
Figure 17B:
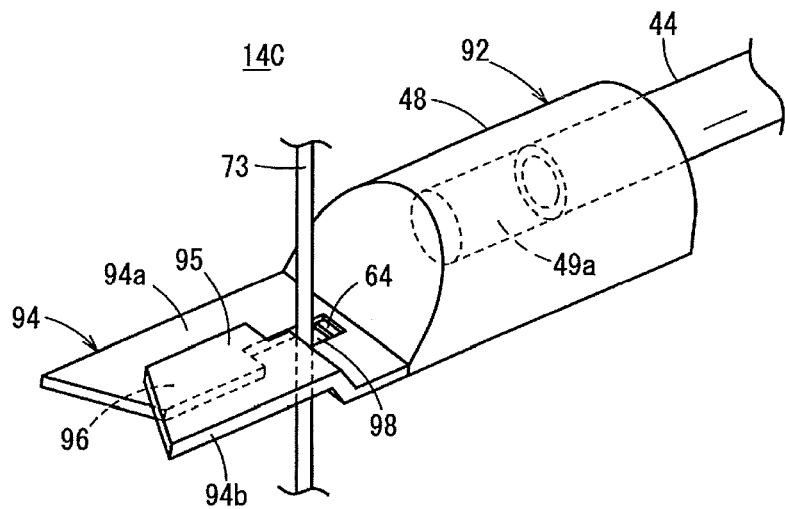
FIG. 17B is a second view for illustrating the capture of the branch vessel by the second dissecting device shown in FIG. 14.

Then, the branch vessel 73 enters between the pair of dissecting portions 94a and 94b, as shown in FIG. 17A, and performs a parallel movement in the width direction relatively toward the groove section 98 side while being sandwiched between the pair of dissecting portions 94a and 94b when the second dissecting device 14C is further moved forward. The branch vessel 73 may be pressed flat during this movement. In this process, the fat 74 is separated from the branch vessel 73. The branch vessel 73 having passed between the pair of dissecting portions 94a and 94b reaches the groove section 98 located on the front side of the base part 48, as depicted in FIG. 17B. The branch vessel 73 can thus be returned into a state of being nearly rectilinear in the height direction. In addition, visibility is enhanced.

The branch vessel 73 that has been guided to the treating section 60 is then stanched (cauterized) by a stanching section 62 and is thereafter cut by a cutting section 64.

When the second dissecting device 14C is inserted along the blood vessel 72, it is thus possible to dissect the tissue (the fat 74) in the living body and to easily capture the branch vessel 73 embedded in the tissue. Since the tissue (the fat 74 or the like) surrounding the branch vessel 73 can be separated by the overlapping part 95 of the pair of dissecting portions 94a and 94b, the tissue can be prevented from clogging on the front side of the base part 48. This makes it possible to easily perform stanching and cutting of the captured branch vessel 73 while observing the branch vessel 73 via an imaging device 17 inserted in an insertion lumen 45.

The tissue in the living body can be easily dissected and the tissue surrounding the branch vessel 73 can be easily separated because the pair of dissecting portions 94a and 94b are plate-shaped. Further, the branch vessel 73 can be smoothly guided while separating the tissue surrounding the branch vessel 73 since the space 96 is formed between the pair of dissecting portions 94a and 94b.

In the second dissecting device 14C, the introducing section 100 (the width of which decreases in the proximal direction) is provided at the distal portion of the dissecting member 92. The introducing section 100 can thus easily draw in the branch vessel 73. Since the overlapping part 95 of the pair of dissecting portions 94a and 94b is provided on the proximal side of the introducing section 100, the tissue surrounding the branch vessel 73 introduced by the introducing section 100 can be separated more effectively.

In the second dissecting device 14C, the branch vessel 73 can be returned into a state of being nearly rectilinear at the groove section 98 (FIG. 17B) because the groove section 98 (which penetrates the dissecting section 94 in the thickness direction of the dissecting section 94) is provided proximal to the overlapping part 95 of the pair of dissecting portions 94a and 94b. Therefore, the branch vessel 73 can be easily visually confirmed by the imaging device 17, and the treatment of stanching and cutting the branch vessel 73 can be easily carried out. Since at least one of the pair of dissecting portions 94a and 94b is provided with the projecting portion 97a (97b) projecting toward the other dissecting portion, the dissecting member 92 having the overlapping part 95 of the pair of dissecting portions 94a and 94b and the groove section 98 on the proximal side of the overlapping part 95 can be realized with a simple configuration.

The detailed description above describes a dissecting device and dissecting method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A dissecting device comprising:
a grasping section comprising an insertion lumen configured to permit an imaging device to be positioned in the insertion lumen, the grasping section being graspable by a user, the grasping section possessing a distal portion;
a dissecting member at the distal portion of the grasping section, the dissecting member being insertable into a living body and movable along a blood vessel to dissect tissue surrounding the blood vessel, the dissecting member extending in a longitudinal direction and possessing a width direction and a height direction;
the dissecting member comprising a base part having a lumen that communicates with the insertion lumen and a dissecting section which extends distally from the base part, the dissecting section being configured to dissect the tissue in the living body when the dissecting member is moved along the blood vessel; and
the dissecting member comprising a blood vessel guide passage configured to accept a branch vessel branched from the blood vessel at the distal portion of the dissecting member and guide the branch vessel toward the base part, wherein the dissecting section possesses a thickness in the height direction and possesses a distal end and a proximal end, the thickness of the dissecting section increasing from the distal end to the proximal end of the dissecting section, the blood vessel guide passage possesses a thickness in the height direction and possesses a distal end and a proximal end, and the thickness of the blood vessel guide passage increases from the distal end to the proximal end of the blood vessel guide passage in proportion to the increase in the thickness of the dissecting section.

2. The dissecting device according to claim 1, wherein the blood vessel guide passage is more narrow than the insertion lumen.

3. The dissecting device according to claim 1, wherein the blood vessel guide passage penetrates the dissecting member in the height direction of the dissecting member.

4. The dissecting device according to claim 1, wherein
the blood vessel guide passage comprises a proximal portion and a distal portion, the blood vessel guide passage possessing a width in the width direction, and
the width of the proximal portion of the blood vessel guide passage is less than the width of the distal portion of the blood vessel guide passage.

5. The dissecting device according to claim 1, wherein the blood vessel guide passage includes:
a first guide passage,
a second guide passage proximal to the first guide passage, the second guide passage being spaced apart from the first guide passage in the width direction of the dissecting member, and
an intermediate guide passage extending between the first guide passage and the second guide passage to connect the first guide passage to the second guide passage so that the first and second guide passages communicate.

6. The dissecting device according to claim 1, wherein the blood vessel guide passage includes a first groove section and a second groove section proximal to the first groove section, the first groove section possessing a distal end and a proximal end, the first groove section and the second groove section each possessing a width, and
the width of the first groove section being greater than the width of the second groove section, the width of the first groove section decreasing from the distal end to the proximal end of the first groove section.

7. The dissecting device according to claim 1, wherein the dissecting member comprises a roof section positioned above the blood vessel guide passage and the dissecting section in the height direction such that the roof section at least partly covers the blood vessel guide passage and the dissecting section, the roof section being configured to permit the branch vessel to pass between the roof section and the dissecting section.

8. The dissecting device according to claim 1, further comprising a treating section at a proximal portion of the blood vessel guide passage, the treating section being configured to stanch and cut the branch vessel.

9. A dissecting device for dissecting tissue surrounding a blood vessel in a living body, the blood vessel including a branch vessel branching outwardly away from the blood vessel, the dissecting device comprising:
an elongated tubular body comprising an insertion lumen configured to permit an imaging device to be positioned in the insertion lumen, the elongated tubular body being graspable by a user, the elongated tubular body possessing a distal portion;

a dissecting member connected to the distal portion of the elongated tubular body, the dissecting member being insertable into the living body and movable along the blood vessel to dissect the tissue surrounding the blood vessel, the dissecting member extending in a longitudinal direction and possessing a lateral direction and a vertical direction;

the dissecting member comprising a base part and two protruding parts extending distally from the base part, the two protruding parts each possessing a distal end and a proximal end, the two protruding parts being spaced apart from one another in the lateral direction to create a blood vessel guide passage between the two protruding parts, the blood vessel guide passage comprising a tapered portion and a straight portion proximal of the tapered portion, the tapered portion possessing a distal end and proximal end and the straight portion possessing a distal end and a proximal end;

one of the two protruding parts possessing an inner surface and an other of the two protruding parts possessing an inner surface opposite the inner surface of the one protruding part, the inner surface of the one protruding part being spaced apart from the inner surface of the other protruding part in the lateral direction;

a distance between the inner surface of the one protruding part and the inner surface of the other protruding part gradually decreasing throughout the tapered portion of the blood vessel guide passage from the distal end of the two protruding parts to the proximal end of the tapered portion;

the distance between the inner surface of the one protruding part and the inner surface of the other protruding part being constant along the straight portion of the blood vessel guide passage from the distal end of the straight portion to the proximal end of the straight portion;

the dissecting member comprising a treating section at the proximal end of the straight portion of the blood vessel guide passage, the treating section comprising two electrodes and a cutting section, the two electrodes being configured to stanch the branch vessel and the cutting section being configured to cut the branch vessel; and the blood vessel guide passage of the dissecting member being configured to accept the branch vessel branched from the blood vessel at the tapered portion of the blood vessel guide passage and guide the branch vessel through the straight portion of the blood vessel guide passage to the treating section when the dissecting member is moved along the blood vessel.

10. The dissecting device according to claim 9, further comprising a first guide member connected to an outer surface of the one protruding part in the lateral direction and a second guide member connected to an outer surface of the other protruding part in the lateral direction, the first and second guide members being taller than the two protruding parts in the vertical direction.

11. The dissecting device according to claim 9, wherein the two protruding parts are each inclined from the distal end to the proximal end in the vertical direction.

12. The dissecting device according to claim 9, wherein
the two electrodes of the treating section each possess a distal-most end,
the cutting section possesses a distal-most end, and the distal-most end of the two electrodes is distal to the distal-most end of the cutting section so that the branch vessel is stanched by the electrodes before being cut by the cutting section.

13. The dissecting device according to claim 9, wherein the dissecting member comprises two distal-most projections, the distal-most projections extending distally beyond the two protruding parts, the distal-most projections being at a bottom of the dissecting member in the vertical direction.

14. The dissecting device according to claim 9, wherein the dissecting member possesses a top and a bottom in the vertical direction, the top of the dissecting member being directly opposite the blood vessel when the dissecting member is moved forward along the blood vessel in the living body, and the two electrodes and the cutting section of the treating section are at the bottom of the dissecting member in the vertical direction.

15. A dissecting method for dissecting tissue surrounding a blood vessel in a living body, the method comprising:
   introducing a dissecting device into the living body by way of an incision, the dissecting device comprising a main body, two protruding portions, a stanching section and a cutting section, the main body extending in a longitudinal direction and possessing a thickness direction, the two protruding portions protruding distally beyond the main body in the longitudinal direction of the main body;
   positioning the dissecting device below the blood vessel in the living body, the stanching section and the cutting section being at a bottom of the dissecting device in the thickness direction of the dissecting device so that the stanching section and the cutting section are below the blood vessel and spaced apart from the blood vessel;
   dissecting the tissue surrounding the blood vessel in the living body by moving the dissecting device forward along the blood vessel while the dissecting device is below the blood vessel, the blood vessel including branch vessels that branch outwardly away from the blood vessel;
   guiding one of the branch vessels toward the stanching section using the two protruding portions;
   stanching the one branch vessel using the stanching section of the dissecting device;
   cutting the one branch vessel from the blood vessel using the cutting section of the dissecting device after the stanching of the one branch vessel;
   introducing a different dissecting device into the living body before the one dissecting device is introduced into the living body, the different dissecting device being configured differently than the one dissecting device;
   positioning the different dissecting device above the blood vessel in the living body;
   dissecting the tissue surrounding the blood vessel in the living body by moving the different dissecting device forward along the blood vessel while the different dissecting device is above the blood vessel; and
   removing the different dissecting device from the living body after the dissecting of the tissue by the different dissecting device.

16. The method according to claim 15, wherein the guiding of the one branch vessel toward the stanching section comprises guiding the one branch vessel along a curved path.

* * * * *